(12) United States Patent
Lu et al.

(10) Patent No.: US 7,754,689 B2
(45) Date of Patent: Jul. 13, 2010

(54) FINGER-1 PEPTIDE ANALOGS OF THE TGF-β SUPERFAMILY

(75) Inventors: Zhijian Lu, Bedford, MA (US); Wei Liu, Lexington, MA (US); Jimin Zhang, Chestnut Hill, MA (US); Paul John Yaworsky, Rockland, MA (US); Stephane H. Olland, Arlington, MA (US); Christopher Todd Brown, Lowell, MA (US); Emily Sheng-ming Shen, West Chester, PA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/809,383

(22) Filed: Jun. 1, 2007

(65) Prior Publication Data

US 2008/0051340 A1    Feb. 28, 2008

Related U.S. Application Data

(60) Provisional application No. 60/810,798, filed on Jun. 2, 2006.

(51) Int. Cl.
| A61K 38/00 | (2006.01) |
| A61K 38/24 | (2006.01) |
| A01N 37/18 | (2006.01) |
| C07K 1/00 | (2006.01) |
| C07K 14/00 | (2006.01) |
| C07H 21/04 | (2006.01) |

(52) U.S. Cl. .................. 514/12; 530/399; 530/350; 530/417; 536/23.5; 514/2

(58) Field of Classification Search .................. None
See application file for complete search history.

(56) References Cited

U.S. PATENT DOCUMENTS

| 4,522,811 | A | 6/1985 | Eppstein et al. |
| 4,879,236 | A | 11/1989 | Smith et al. |
| 5,024,841 | A | 6/1991 | Chu et al. |
| 5,162,222 | A | 11/1992 | Guarino et al. |
| 5,171,579 | A | 12/1992 | Ron et al. |
| 5,206,028 | A | 4/1993 | Li |
| 5,256,418 | A | 10/1993 | Kemp et al. |
| 6,620,406 | B1 | 9/2003 | Wozney et al. |
| 2002/0143170 | A1 | 10/2002 | Ni et al. |
| 2003/0235536 | A1 | 12/2003 | Blumberg et al. |

FOREIGN PATENT DOCUMENTS

| EP | 0691349 | 1/1996 |
| WO | WO 93/00050 | 1/1993 |
| WO | WO 94/06463 | 3/1994 |
| WO | WO 96/40771 | 12/1996 |

(Continued)

OTHER PUBLICATIONS

PCT App. No. US2007/013053 Invitation to Pay Additional Fees, Jan. 10, 2008.

(Continued)

*Primary Examiner*—Cherie M Woodward

(57) ABSTRACT

Members of the TGF-β superfamily and peptide fragments based on member proteins are employed to purify solutions containing member proteins or as therapeutics.

8 Claims, 14 Drawing Sheets

FOREIGN PATENT DOCUMENTS

| WO | WO 02/077006 | 10/2002 |
|---|---|---|
| WO | WO 2004/014940 | 2/2004 |
| WO | WO 2005/089826 | 9/2005 |

OTHER PUBLICATIONS

Cain et al., "Endothelin-1 Receptor Binding Assay for High Throughput Chemical Screening," *Cardiovasc. Pharm.* 17:S150-S151 (1991).

Database abcam [Online] "BMP7 antibody (ab27569) datasheet" XP002456044 retrieved from http://www.abcam.com accession No. ab27569, Oct. 19, 2007.

Database reseachd [Online] Rabbit anti-human BMP2, Feb. 22, 2005, cat # RDI-BMP2ABRX, XP002456045, retrieved from http://www.researchd.com.

Gerard, "Purification of Glycoproteins," *Methods in Enzymology* 182:529-539 (1990).

Gref et al., "Biodegradable Long-Circulating Polymeric Nanospheres," *Science* 263:1600-1603 (1994).

Higuchi et al., Microtiter Plate Radiorecptor Assay for Tumor Necrosis Factor and Its Receptors in Large Numbers of Samples, *Anal. Biochem.* 204:53-58 (1992).

Kohno et al., "Refolding of Recombinant Proteins," *Meth. Enzym.* 185:187-195 (1990).

Ruppert et al., "Human bone morphogenetic protein 2 contains a heparin-binding site which modifies its biological activity," *Eur. J. Biochem*, 237:295-302 (1996).

Scheufler et al., "Crystal Structure of Human Bone Morphogenetic Protein-2 at 2.7 Å Resolution," *J. Mol. Biol.* 287:103-115 (1999).

Sulkowski, "Purification of proteins by IMAC," *Trends in Biochem* 3:1-7 (1985).

Williams, "Receptor Binding in the Drug Discovery Process," *Med Res. Rev.* 11:147-184 (1991).

Young et al., "Production of biopharmaceutical proteins in the milk of transgenic dairy animals," *BioPharm* 10(6):34-38 (1997).

SEQUENCE LISTING

```
<160> NUMBER OF SEQ ID NOS: 23

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Asp Val Gly Trp Asn Asp Trp Ile Val Ala Pro Pro Gly Tyr His
  1               5                   10                  15

Ala Phe Tyr Cys His Gly Glu Lys
```

```
<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Glu Leu Gly Trp Asp Asp Trp Ile Ile Ala Pro Leu Asp Tyr Glu
 1               5                  10                  15

Ala Tyr His Cys Glu Gly Leu Cys
            20

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Asp Val Gly Trp Asn Asp Trp Ile Val Ala Pro Pro Gly Tyr His
 1               5                  10                  15

Ala Phe Tyr Cys His Gly Glu Cys
            20

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Asp Val Gly Ala Asn Asp Trp Ile Val Ala Pro Pro Gly Tyr His
 1               5                  10                  15

Ala Phe Tyr Cys His Gly Glu Cys
            20

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Asp Val Gly Ala Asn Asp Trp Ile Val Ala Pro Pro Gly Tyr His
 1               5                  10                  15

Ala Phe Tyr Cys His Gly Glu Lys
            20

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Ser Asp Val Gly Trp Asn Asp Trp Ile Val Ala Pro Pro Gly Tyr His
 1               5                  10                  15

Ala Phe Tyr Cys His Ala Glu Cys
            20

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Asp Val Gly Trp Asn Asp Trp Ile Val Ala Pro Pro Gly Tyr His
 1               5                  10                  15

Ala Phe Tyr Cys His Ala Glu Lys
            20

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Asp Val Gly Ala Asn Asp Trp Ile Val Ala Pro Pro Gly Tyr His
 1               5                  10                  15

Gly Phe Tyr Cys His Gly Glu Cys
            20

<210> SEQ ID NO 9
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Asp Val Gly Ala Asn Asp Trp Ile Val Ala Pro Pro Gly Tyr His
 1               5                  10                  15

Gly Phe Tyr Cys His Gly Glu Lys
            20

<210> SEQ ID NO 10
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Tyr Val Asp Phe Ser Asp Val Gly Trp Asn Asp Trp Ile Val Ala
 1               5                  10                  15

Pro Pro Gly Tyr His Ala Phe Tyr
            20

<210> SEQ ID NO 11
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Tyr Val Asp Phe Ser Asp Val Gly Ala Asn Asp Trp Ile Val Ala
 1               5                  10                  15

Pro Pro Gly Tyr His Ala Phe Tyr
            20

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Tyr Val Asp Phe Ser Asp Val Gly Trp Asn Asp Trp Ile Val Ala
 1               5                  10                  15

Pro Pro Gly Tyr His Gly Phe Tyr
            20

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Glu Leu Gly Trp Asp Asp Trp Ile Ile Ala Pro Leu Asp Tyr Glu
 1               5                  10                  15

Ala Tyr His Cys Glu Gly Leu Lys
            20

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Glu Leu Gly Trp Asp Asp Trp Ile Ile Ala Pro Leu Asp Tyr Glu
 1               5                  10                  15

Ala Tyr His Cys Glu Gly Leu Lys
            20

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Asp Ile Gly Trp Ser Glu Trp Ile Ile Ser Pro Lys Ser Phe Asp
 1               5                  10                  15
```

```
Ala Tyr Tyr Cys Ser Gly Ala Cys
            20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Asp Ile Gly Trp Ser Glu Trp Ile Ile Ser Pro Lys Ser Phe Asp
1               5                   10                  15

Ala Tyr Tyr Cys Ser Gly Ala Lys
            20

<210> SEQ ID NO 17
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylation

<400> SEQUENCE: 17

Ser Asp Val Gly Trp Asn Asp Trp Ile Val Ala Pro Pro Gly Tyr His
1               5                   10                  15

Ala Phe Tyr Ser His Gly Glu Lys
            20

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylation

<400> SEQUENCE: 18

Ser Asp Val Gly Trp Asn Asp Trp Ile Val Ala Pro Pro Gly Tyr His
1               5                   10                  15

Ala Phe Tyr Cys His Gly Glu Lys
            20

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylation

<400> SEQUENCE: 19

Glu Leu Gly Trp Asp Asp Trp Ile Ile Ala Pro Leu Asp Tyr Glu Ala
1               5                   10                  15

Tyr His Ser Glu Gly Leu Lys
            20

<210> SEQ ID NO 20
```

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylation

<400> SEQUENCE: 20

Arg Asp Leu Gly Trp Gln Asp Trp Ile Ile Ala Pro Glu Gly Tyr Ala
 1               5                  10                  15

Ala Phe Tyr Ser Asp Gly Glu Lys
            20

<210> SEQ ID NO 21
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylation

<400> SEQUENCE: 21

Leu Tyr Val Asp Phe Ser Asp Val Gly Trp Asn Asp Trp Ile Val Ala
 1               5                  10                  15

Pro Pro Gly Tyr His Ala Phe Tyr Ser His Gly Glu Lys
            20                  25

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylation

<400> SEQUENCE: 22

Leu Tyr Val Ser Asp Val Gly Trp Asn Asp Trp Ile Val Lys
 1               5                  10

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylation

<400> SEQUENCE: 23

Val Ala Pro Pro Gly Tyr His Ala Phe Tyr Ser His Gly Glu Lys
 1               5                  10                  15
```

FINGER-1 PEPTIDE ANALOGS OF THE TGF-β SUPERFAMILY

CROSS REFERENCE TO RELATED APPLICATIONS

This application claims priority to United States Provisional Patent Application No. 60/810,798, filed Jun. 2, 2006, which is hereby incorporated by reference in its entirety.

FIELD OF THE INVENTION

This invention relates to the use of peptides and proteins of the TGF-β superfamily and their mutants.

BACKGROUND OF THE INVENTION

Natural regulators of cellular growth, differentiation and function have provided important pharmaceuticals, clinical and laboratory tools, and targets for therapeutic intervention. A variety of such regulators have been shown to have profound effects on basic cellular differentiation and developmental pathways. The transforming growth factor beta (TGF-β) superfamily is a large family of multifunctional proteins that regulate a variety of cellular functions including cellular proliferation, migration, differentiation and apoptosis. TGF-β, the founding member, has been shown to play a variety of roles ranging from embryonic pattern formation to cell growth regulation in adult tissues. TGF-β exerts its biological functions by signal transduction cascades that ultimately activate and/or suppress expression of a set of specific genes. Other TGF-β superfamily members include the TGF-β family, growth differentiation factors (GDFs), activins, inhibins, Bone Morphogenic Proteins (BMPs, and other related ligands. BMP-mediated signal transduction is important for a variety of normal processes, including bone growth and the function of the nervous system, eyes and organs such as kidneys. BMPs have diverse biological activities in different biological contexts, including the induction of cartilage, bone and connective tissue, and roles in kidney, tooth, gut, skin and hair development.

BMPs can be produced in the laboratory, however, there are few convenient procedures for purification of these materials and development of purification methods has often been ad hoc and time consuming, with purification processes sometimes taking up to 6 months to develop. Accordingly it is desired to have more efficient methods for purifying BMPs and other members of the TGF-β superfamily.

DEFINITIONS

As used herein and in the appended claims, the singular forms "a", "an", and "the" include the plural reference unless the context clearly indicates otherwise. Thus, for example, a reference to "a cell" includes a plurality of such cells, and a reference to "an antibody" is a reference to one or more antibodies and equivalents thereof known to those skilled in the art, and so forth.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example, thio-uracil, thio-guanine, and fluoro-uracil, or containing carbohydrate, or lipids.

Polynucleotides for use with embodiments of the invention may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., Nucl. Acids Res., 16, 3209, (1988), methylphosphonate oligonucleotides can be prepared by use of controlled pore glass polymer supports (Sarin et al., Proc. Natl. Acad. Sci. U.S.A. 85, 7448-7451, (1988), etc. A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, Nature, 290, 304-310, (1981), the promoter contained in the 3' long terminal repeat of Rous sarcoma virus, Yamamoto et al., Cell, 22, 787-797, (1980), the herpes thymidine kinase promoter, Wagner et al., Proc. Natl. Acad. Sci. U.S.A. 78, 1441-1445, (1981), the regulatory sequences of the metallothionein gene Brinster et al., Nature 296, 39-42, (1982), etc. Any type of plasmid, cosmid, yeast artificial chromosome or viral vector can be used to prepare the recombinant DNA construct that can be introduced directly into the tissue site. Alternatively, viral vectors can be used which selectively infect the desired tissue, in which case administration may be accomplished by another route (e.g., systemically).

The polynucleotides may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

"Identity" or "similarity", as known in the art, are relationships between two or more polypeptide or two or more polynucleotide sequences as determined by comparing the sequences. In the art, identity also means the degree of sequence relatedness between polypeptide sequences as determined by the match between strings of such sequences. Both identity and similarity can be readily calculated by known methods such as those described in: Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991. Methods commonly employed to determine identity or similarity between sequences include, but are not limited to, those disclosed in Carillo, H., and Lipman, D., SIAM J Applied Math., 48:1073 (1988). Methods to determine identity and similarity are codified in publicly available computer programs. Preferred computer program methods to determine identity and similarity between two sequences include, but are not limited to, GCG program package, Devereux, J., et al., Nucleic Acids Research, 12(1), 387 (1984)), BLASTP, BLASTN, and FASTA Atschul, S. F. et al., J Molec. Biol., 215, 403 (1990)).

"Homologous" refers to the degree of sequence similarity between two polymers (i.e. polypeptide molecules or nucleic acid molecules). The homology percentage figures referred to herein reflect the maximal homology possible between the two polymers, i.e., the percent homology when the two polymers are so aligned as to have the greatest number of matched (homologous) positions.

The term "percent homology" refers to the extent of amino acid sequence identity between polypeptides. The homology between any two polypeptides is a direct function of the total number of matching amino acids at a given position in either sequence, e.g., if half of the total number of amino acids in either of the sequences are the same then the two sequences are said to exhibit 50% homology.

The term "fragment", "analog", and "derivative" when referring to polypeptides refers to a polypeptide which may retain essentially the same biological function or activity as the original polypeptide. Thus, an analog may include a precursor protein that can be activated by cleavage of the precursor protein portion to produce an active mature polypeptide. The fragment, analog, or derivative of the polypeptide may be one in which one or more of the amino acids are substituted with conserved or non-conserved amino acid residues and such amino acid residues may or may not be the ones encoded by the genetic code, or the ones in which one or more of the amino acid residues include a substituent group, or the ones in which the polypeptide is fused with a compound such as polyethylene glycol to increase the half-life of the polypeptide, or the ones in which additional amino acids are fused to the polypeptide such as a signal peptide or a sequence such as polyhistidine tag which is employed for the purification of the polypeptide or the precursor protein. Such fragments, analogs, or derivatives are deemed to be within the scope of the present invention.

The term "polypeptide" refers to a polymer of amino acids without regard to the length of the polymer; thus, "peptides," "oligopeptides", and "proteins" are included within the definition of polypeptide and used interchangeably herein. This term also does not specify or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, proteins—structure and molecular properties, 2nd Ed., T. E. Creighton, W. H. Freeman and Company, New York (1993); posttranslational covalent modification of proteins, b. c. Johnson, Ed., Academic Press, New York, pgs. 1-12, 1983; Seifter et al., Meth Enzymol 182:626-646, 1990; Rattan et al., Ann NY Acad Sci 663:48-62, 1992). Also included within the definition are polypeptides which contain one or more analogs of an amino acid (including, for example, non-naturally occurring amino acids, amino acids which only occur naturally in an unrelated biological system, modified amino acids from mammalian systems, stereoisomers of various amino acids, etc.), polypeptides with substituted linkages, as well as other modifications known in the art, both naturally occurring and non-naturally occurring. The term "polypeptide" may also be used interchangeably with the term "protein" or "peptide".

The term "finger-1 peptide analog" refers to an oligopeptide that is at least 75% homologous to a portion of the finger-1 region of a member of the TGF-beta superfamily. In some embodiments, the finger-1 peptide analog is at least 80%, at least 85%, at least 90%, or at least 95% homologous to the wild type sequence. In certain embodiments, the oligopeptide includes at least 8 amino acid residues, at least 16 amino acid residues, or at least 24 amino acid residues. Finger-1 peptide analogs may be mutants in which one or more amino acids have been altered or deleted and may include non-natural or modified amino acid residues.

The term "peptide" refers to any polymer of two or more amino acids, wherein each amino acid is linked to one or two other amino acids via a peptide bond (—CONH—) formed between the $NH_2$ and the COOH groups of adjacent amino acids. In one embodiment, the amino acids are naturally occurring amino acids, particularly alpha-amino acids of the L-enantiomeric form. However, other amino acids, enantiomeric forms, and amino acid derivatives may be included in a peptide. Peptides include "polypeptides," which, upon hydrolysis, yield more than two amino acids. Polypeptides may include proteins, which typically comprise 50 or more amino acids.

The polypeptides according to embodiments of the present invention may be provided in an isolated form, and may be purified to homogeneity. The polypeptides and polynucleotides in certain instances are at least 90% pure, at least 95% pure, at least 98% pure, or at least 99% pure.

The term "polypeptide" refers to a polymer of amino acids without regard to the length of the polymer; thus, "peptides," "oligopeptides", and "proteins" are included within the definition of polypeptide and used interchangeably herein. This term also does not specify or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, proteins—structure and molecular properties, 2nd Ed., T. E. Creighton, W. H. Freeman and Company, New York (1993); posttranslational covalent modification of proteins, b. c. Johnson, Ed., Academic Press, New York, pgs. 1-12, 1983; Seifter et al., Meth Enzymol 182:626-646, 1990; Rattan et al., Ann NY Acad Sci 663:48-62, 1992). Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring. The term "polypeptide" may also be used interchangeably with the term "protein" or "peptide".

The term "peptide" refers to any polymer of two or more amino acids, wherein each amino acid is linked to one or two other amino acids via a peptide bond (—CONH—) formed between the NH2 and the COOH groups of adjacent amino acids. Preferably, the amino acids are naturally occurring amino acids, particularly .alpha.-amino acids of the L-enantiomeric form. However, other amino acids, enantiomeric forms, and amino acid derivatives may be included in a peptide. Peptides include "polypeptides," which, upon hydrolysis, yield more than two amino acids. Polypeptides may include proteins, which typically comprise 50 or more amino acids.

The term "isolated" means that the material is removed from its original or native environment (e.g., the natural environment if it is naturally occurring). Therefore, a naturally-occurring polypeptide present in a living animal is not isolated, but the same polypeptide, separated by human intervention from some or all of the coexisting materials in the natural system, is isolated. Polypeptides could be part of a composition, and still be isolated in that such vector or composition is not part of the environment in which it is found in nature. Similarly, the term "substantially purified" refers to a substance, which has been separated or otherwise removed, through human intervention, from the immediate chemical environment in which it occurs in nature. Substantially purified polypeptides may be obtained or produced by any of a number of techniques and procedures generally known in the field.

The term "purification" refers to increasing the specific activity or concentration of a particular polypeptide or polypeptides in a sample. In one embodiment, specific activity is expressed as the ratio between the activity of the target polypeptide and the concentration of total polypeptide in the sample. In another embodiment, specific activity is expressed as the ratio between the concentration of the target polypeptide and the concentration of total polypeptide. Purification methods include but are not limited to dialysis, centrifugation, and column chromatography techniques, which are well-known procedures to those of skill in the art. See, e.g., Young et al., 1997, "Production of biopharmaceutical proteins in the milk of transgenic dairy animals," BioPharm 10(6): 34-38.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

The term "isolated" means that the material is removed from its original or native environment (e.g., the natural environment if it is naturally occurring). Therefore, a naturally-occurring polynucleotide or polypeptide present in a living animal is not isolated, but the same polynucleotide or polypeptide, separated by human intervention from some or all of the coexisting materials in the natural system, is isolated. For example, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA and combined with carbohydrate, lipid, protein or other materials. Such polynucleotides could be part of a vector and/or such polynucleotides or polypeptides could be part of a composition, and still be isolated in that such vector or composition is not part of the environment in which it is found in nature. Similarly, the term "substantially purified" refers to a substance, which has been separated or otherwise removed, through human intervention, from the immediate chemical environment in which it occurs in Nature. Substantially purified polypeptides or nucleic acids may be obtained or produced by any of a number of techniques and procedures generally known in the field.

The terms "substantially pure" and "isolated" are not intended to exclude mixtures of polypeptides with substances that are not associated with the polypeptides in nature.

General methods for expressing and recovering foreign protein produced by a mammalian cell system are provided by, for example, Etcheverry, "Expression of Engineered Proteins in Mammalian Cell Culture," in Protein Engineering: Principles and Practice, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in DNA Cloning 2: Expression Systems, 2nd Edition, Glover et al. (eds.), pages 59-92 (Oxford University Press 1995). Transformation of insect cells and production of foreign polypeptides therein is disclosed by Guarino et al., U.S. Pat. No. 5,162,222 and WIPO publication WO94/06463. Methods for isolating recombinant proteins from a baculovirus system are also described by Richardson (ed.), "Baculovirus Expression Protocols" (The Humana Press, Inc. 1995). In one embodiment, the polypeptides of the invention can be expressed using a baculovirus expression system (see, Luckow et al., Bio/Technology, 1988, 6, 47, "Baculovirus Expression Vectors: a Laboratory Manual", O'Rielly et al. (Eds.), W. H. Freeman and Company, New York, 1992, U.S. Pat. No. 4,879,236, each of which is incorporated herein by reference in its entirety). In addition, the MAXBAC™ complete baculovirus expression system (Invitrogen) can, for example, be used for production in insect cells.

The polypeptides according to various embodiments of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, Trends in Biochem. 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), Meth. Enzymol. 182:529 (1990)). Within additional embodiments of the invention, a fusion of the polypeptide of interest and an affinity tag (e.g., maltose-binding protein, an immunoglobulin domain) may be constructed to facilitate purification.

The term "in vitro" refers to an artificial environment and to reactions or processes that occur within an artificial environment. In vitro environments include, but are not limited to, test tubes and cell cultures. The term "in vivo" refers to the natural environment (e.g., an animal or a cell) and to processes or reaction that occur within a natural environment.

The term "phenotype" refers to the observable character of a cell or an organism. Such observable character can involve the physical appearance, as well as a level of particular physiological compositions present in the cell or organism.

The term "signal transduction pathway" refers to the molecules that propagate an extracellular signal through the cell membrane to become an intracellular signal. This signal can then stimulate a cellular response. The polypeptide molecules involved in signal transduction processes may be receptor and non-receptor protein tyrosine kinases.

"Receptor" refers to a molecular structure within a cell or on the surface of the cell that is generally characterized by the selective binding of a specific substance.

The terms "compound" or "agent" are used interchangeably herein to refer to a compound or compounds or composition of matter which, when administered to a subject (human or animal) induces a desired pharmacologic and/or physiologic effect by local and/or systemic action.

The term "subject" refers to any mammal, including a human, or non-human subject. Non-human subjects can include experimental, test, agricultural, entertainment or companion animals. A subject may be a human. A subject may be a domesticated animal, such as a dog, cat, cow, goat, sheep, pig, etc., A subject may be an experimental animal, such as a mouse, rat, rabbit, monkey, etc.

As used herein, the term "small molecule" is used to refer to molecules, whether naturally-occurring or artificially created (e.g., via chemical synthesis), that have a relatively low molecular weight. In many embodiments, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R.§§330.5, 331 through 361, and 440 through 460; drugs for veterinary use listed by the FDA under 21 C.F.R.§§ 500 through 589, incorporated herein by reference, are all considered acceptable for use in accordance with the present invention.

SUMMARY OF THE INVENTION

In one aspect, the invention is a chromatography media comprising a chromatography resin derivatized with a peptide that is at least 75% homologous to a portion of a protein that is a member of the TGF-β superfamily. The member may be a TGF-β, a growth differentiation factor (GDF), a bone morphogenic protein, an activin, or an inhibin. The peptide may be a substantially complete molecule of the protein. The peptide may be at least 75%, at least 80%, at least 85%, at least 90%, or at least 95% homologous to a portion of a finger-1 peptide from the member.

In another aspect, the invention is a method of purifying a sample including a growth factor that is a member of the TGF-β superfamily. The method includes providing a chromatography column containing a chromatography resin derivatized with a peptide that is at least 75% homologous to a portion of a protein that is a member of the TGF-β superfamily, loading the column with the sample under conditions in which the growth factor tends to aggregate, and eluting the growth factor from the column under conditions in which the growth factor tends to solubilize. The peptide need not be a portion of the growth factor.

In another aspect, the invention is a chromatography media comprising a chromatography resin derivatized with a peptide that is at least 75% homologous to a portion of a finger-1 peptide of a member of the TGF-β superfamily.

In another aspect, the invention is a solution of bone morphogenic proteins in a solvent comprising a predetermined concentration of a predetermined bone morphogenic protein, and a predetermined concentration of a peptide that is at least 75% homologous to a portion of a finger-1 peptide of a member of the TGF-β superfamily. The member of the TGF-β superfamily may, but need not, be the predetermined bone morphogenic protein.

In another aspect, the invention is a method of stabilizing a solution of bone morphogenic protein. The method includes adding a predetermined concentration of a peptide that is at least 75% homologous to a portion of a finger-1 peptide of a member of the TGF-β superfamily to a solution of the bone morphogenic protein.

In another aspect, the invention is a composition including a peptide that is at least 75% homologous to a portion of a finger-1 peptide of a member of the TGF-β superfamily to a solution of the bone morphogenic protein and a carrier. The carrier may be a gel, a polymer, demineralized bone, a suture, a surgical mesh, a ceramic, a micelle, or any combination of the above. For example, the carrier may include a buffer solution, collagen, a collagen sponge, or a cellulose-based material. Alternatively or in addition, the carrier may include one or more of alkylcellulose (including hydroxyalkylcellulose), including methylcellulose, ethylcellulose, hydroxyethylcellulose, hydroxypropylcellulose, hydroxypropyl-methylcellulose, and carboxymethylcellulose. In some embodiments, the carrier may include polyglyconate, hyaluronic acid, polylactic acid, poly(ethylene glycol), sodium alginate, poly(ethylene glycol), polyoxyethylene oxide, carboxyvinyl polymer, and poly(vinyl alcohol). The peptide may be stabilized by one or more of a conjugated poly(propylene glycol), a conjugated sialyl group, a conjugated polysialyl chain, incorporation of modified amino acids, incorporation of non-natural amino acids, interchain covalent links, intrachain covalent links, interchain non-covalent links, interchain non-covalent links, and a presentation enhancer.

In another aspect, the invention is an assay method comprising contacting a population of cells with a peptide that is at least 75% homologous to a portion of a finger-1 peptide of a member of the TGF-β superfamily and detecting a change in a characteristic of the cells when the peptide is present versus when the peptide is absent. The characteristic may be selected from a stage in a cell cycle, expression of a gene or protein, a visible or measurable phenotypic characteristic, a level of expression of a gene or protein, and the transduction of a signal from a receptor. The method may further include contacting the cells with a protein that is a member of the TGF-β superfamily. The peptide may be constrained in a particular configuration.

In another aspect, the invention is an assay method comprising contacting a population of receptors with a known quantity of a peptide that is at least 75% homologous to a finger-1 peptide of a portion of a member of the TGF-β superfamily and detecting a change in the quantity of peptide that is not bound to the receptors. The receptors may be contacted with a protein that is a member of the TGF-β superfamily.

In another aspect, the invention is a composition comprising a peptide that is at least 75% homologous to a portion of a finger-1 peptide of a member of the TGF-β superfamily and an agent that increases the in vivo stability of the peptide with respect to elimination from an animal.

In another aspect, the invention is an assay method comprising contacting a population of receptors with a known quantity of a peptide that is at least 75% homologous to a finger-1 peptide of a portion of a member of the TGF-β superfamily and a small molecule and detecting a change in the quantity of peptide that is not bound to the receptors when the small molecule is present versus when the small molecule is absent.

BRIEF DESCRIPTION OF THE DRAWINGS

The invention is described with reference to the several figures of the drawing, in which.

DETAILED DESCRIPTION OF CERTAIN PREFERRED EMBODIMENTS

Figure 1:
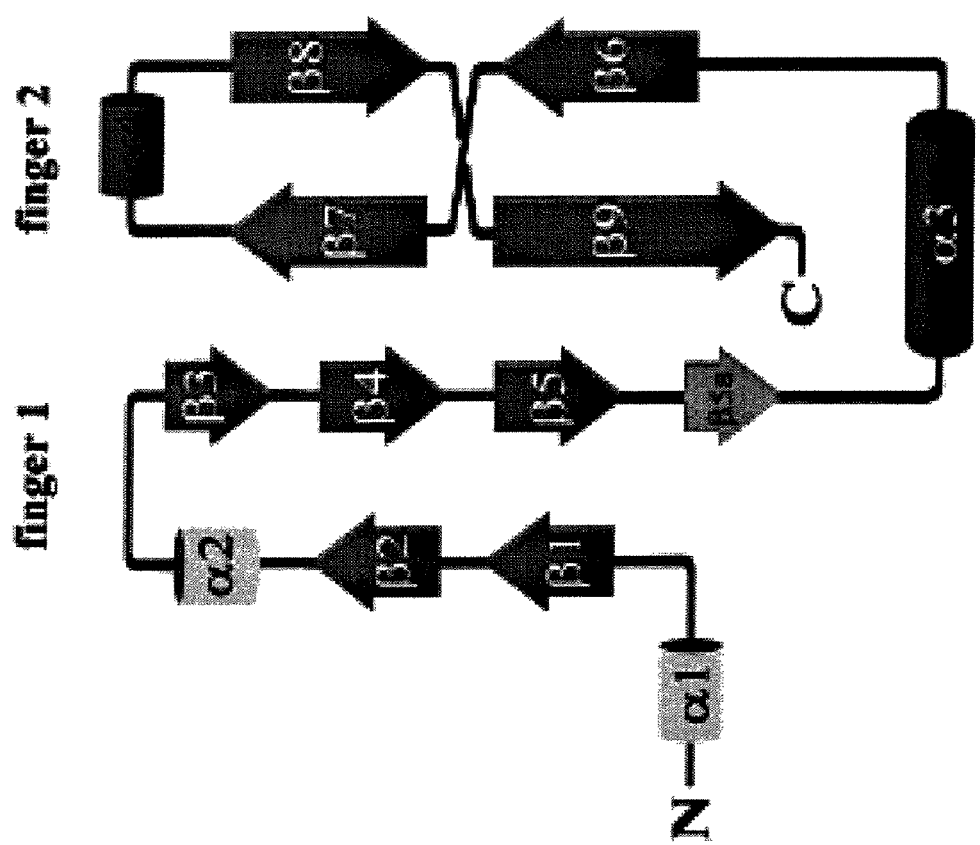
FIG. 1 is a schematic of BMP-2, showing the finger regions and various helices and β-sheets (Adapted from Scheufler, et al., *J. Mol. Bio.* (1999), 287: 103-115).

In certain embodiments, a portion of the first finger peptide of a BMP is employed to perform affinity chromatography. The secondary structure of members of the TGF-β superfamily is typified by two antiparallel β-sheets separated by a four turn alpha-helix about perpendicular to the strands in the β-sheets. The second of the two β-sheets has a twisted crossover conformation. The structure is often stabilized by a cysteine knot formed as pairs of cysteine residues form intrachain disulfide bridges. Some members of the TGF-β superfamily are further stabilized by the formation of dimers or higher order multimers. FIG. 1 shows the finger regions and the various helices and β-sheets in an exemplary BMP, BMP-2. For many members of the TGF-β superfamily, the β-sheets can be subdivided into nine β-strands. Other features of BMP-2, such as the alpha-2 helix and the β5a strand, are not found in all members of the TGF-β superfamily, some of which may exhibit additional helices and β-strands that are not found in BMP-2 (Scheufler, et al., *J. Mol. Bio.* (1999), 287: 103-115).

Exemplary members of the TGF-β superfamily include but are not limited to BMP2, BMP3, BMP4, BMP5, BMP6, BMP7, BMP8A, BMP8B/OP2, BMP9/GDF2, BMP10, BMP11/GDF11, BMP12/GDF7, BMP13/GDF6, BMP15, BMP16/nodal, BMP17/LeftyB, BMP18/Lefty2/TGF β4, α inhibin, Inhibin β3A, Inhibin βB, Inhibin βC, Inhibin βE/BMP14/GDF12, TGF β1, TGF β2, TGF β3, GDF1, GDF3/Vgr-2, GDF5, GDF8, GDF9, GDF10/BMP3B, GDF15, artemin, GDNF (glial derived neurotrophic factor), Mullerian duct inhibiting substance, neuturin, and persephin. While the discussion below focuses on BMP, the teachings may be applied to any member of the TGF-β superfamily.

BMPs tend to aggregate and precipitate at physiological pH (Ruppert, et al., 1996 *Eur J Biochem.* 1996, 237(1):295-302). In some embodiments, this tendency was exploited by linking whole BMPs or finger-1 peptide analogs derived from their first finger domains as ligands linked to sepharose beads to produce affinity chromatography resins.

Chromatography

Figure 2:
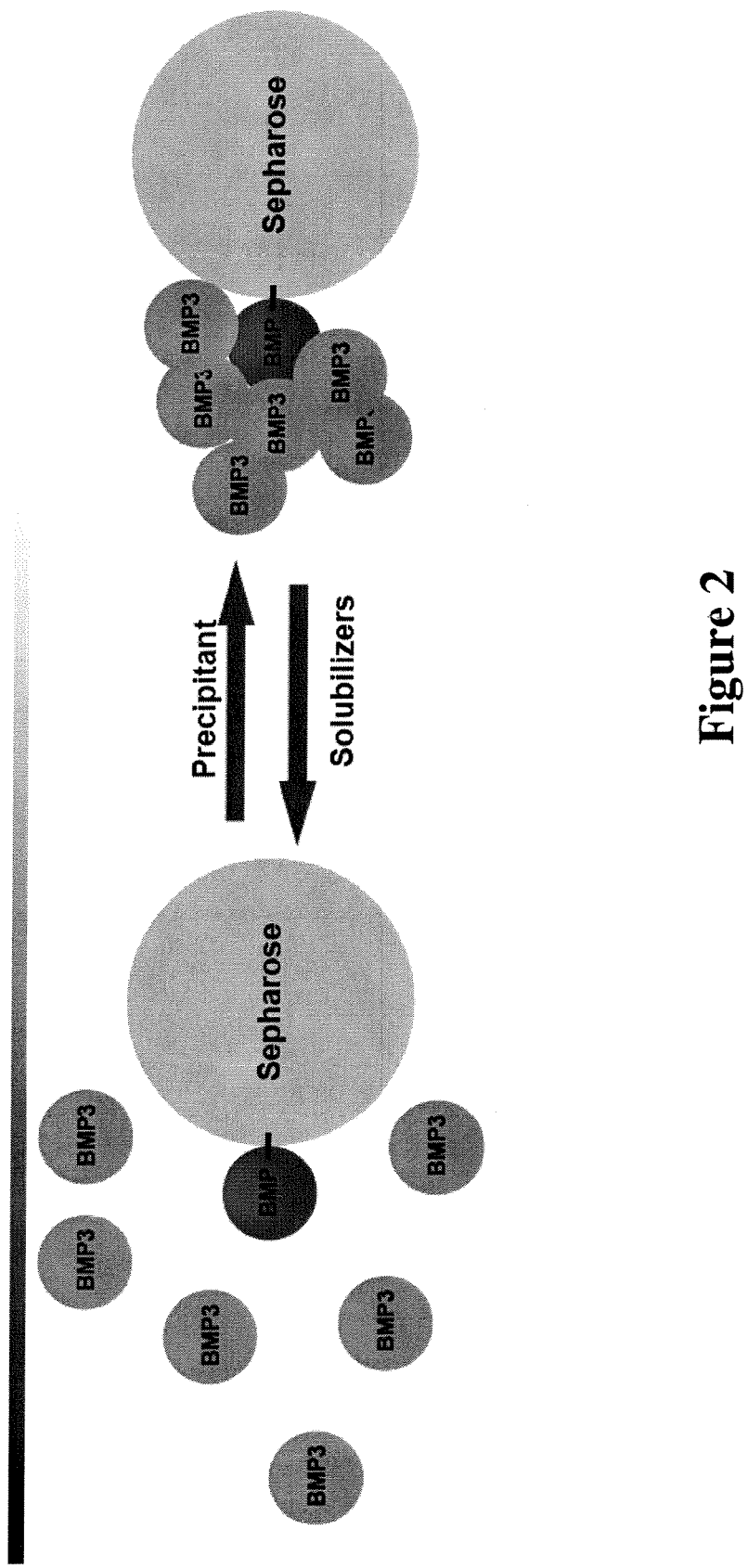
FIG. 2 is a schematic of an affinity chromatography method according to an exemplary embodiment of the invention.

FIG. 2 illustrates the principles of affinity purification according to certain embodiments of the invention. A BMP or finger-1 peptide analog is immobilized on chromatography media. Exemplary media include agarose (e.g., Sepharose™), polystyrene, silica, dextran, and acrylamide. The media are then slurried into a column according to techniques known to those of skill in the art. The column is loaded with a solution containing a BMP under conditions that favor precipitation of BMP. In one embodiment, BMPs are loaded onto the column from CHO-conditioned media containing either dextran sulfate or heparin, e.g., 100 micrograms/milliliter at physiological pH. In some embodiments, the solution may also include 1.2M NaCl. Other impurities can be washed off the column while the BMP remains aggregated on the column. The BMP are then washed off the column under conditions that promote solvation. One skilled in the art will recognize that the ionic strength and pH of the loading solvent may be optimized for various combinations of immobilized finger-1 peptide analogs and materials being purified.

In some embodiments, additives may be used to optimize the solubility or insolubility of the material being purified. For example, dextran sulfate or heparin may be added to a culture medium to favor solubilization of the BMP while it is being expressed and secreted by the cells. Prior to loading onto the column, Conditioned Medium may be adjusted to a high ionic strength to promote efficient capture and/or aggregation during the chromatography process.

Exemplary BMP solubilizers are known to those of skill in the art and include but are not limited to acetic acid, trifluoroacetic acid, hydrochloric acid, alcohols, acetonitrile, propylene glycol, glycerol, Tween-80, CHAPS (3-((3-Cholamidopropyl)dimethylammonio)-1-Propanesulfonic Acid), L-arginine, 6M urea, and 6M Guanidine HCl. One skilled in the art will recognize that these solvents vary in their aggressiveness with respect to solubilizing BMP. In certain embodiments, BMP are eluted with a 500 mM solution of arginine or 50 mM acetic acid.

Exemplary BMP precipitants are known to those of skill in the art and include but are not limited to solvents with pH greater than about 5, salt solutions including, for example, sodium chloride, phosphate salts, sulfate salts of ammonium and sodium, and citrate. The concentration of sodium chloride to promote precipitation depends on the pH of the solution. Some TGF-β proteins will precipitate in solutions of high salt concentration and low pH, or vice versa. One skilled in the art will recognize how to optimize the salt concentration and pH to obtain desired precipitation characteristics for particular proteins.

Fragments of BMP finger peptides may be employed instead of the entire finger region. The particular sequence used for chromatography or the applications described below may have at least 8, at least 16, or at least 24 amino acid residues. The sequence may be at least 75%, at least 80%, at least 85%, at least 90%, or at least 95% homologous to the corresponding region of the native protein. In some embodiments, mutants may be formed with serine residues in place of cysteine residues in the native sequence. This can reduce cross-linking between peptide chains on the sepharose beads, which may interfere with nucleation of BMP aggregates.

Modifications to the peptide sequence may also be made to improve attachment of the peptide to the substrate. For example, lysine-terminated peptides will easily attach to the chromatography beads through formation of amide bonds. If the natural sequence of the desired peptide is not already lysine-terminated, it may be modified to add the lysine residue. Alternatively or in addition, the N-terminal of the peptide may be amidated and the C-terminal acetylated to ensure that only one end of the peptide will attach to the substrate bead. In an alternative embodiment, a spacer may be interposed between the peptide and the substrate bead. The spacer provides additional conformational flexibility to the peptide, allowing it more freedom to achieve the optimal secondary structure for nucleating peptide aggregates. The spacer may be a simple organic chain or may be a non-binding amino acid sequence. The sequence may be an oligomer of one or two amino acids or may exhibit at least partial homology to a non-binding portion of a protein that is a member of the TGFβ superfamily or some other protein. Alternatively or in addition, a spacer may have a portion that exhibits partial homology to a portion of a protein that is a member of the TGFβ superfamily and a portion that does not. In some embodiments, the effectiveness of the bound peptide may vary depending on whether the free end is the C-terminal or the N-terminal. Individual amino acids may also be deleted, modified as described herein or according to other methods known to those of skill in the art, or replaced.

BMP Solution Stabilizers

In some embodiments, finger-1 peptide analogs may be used to stabilize solutions of BMPs in various pharmaceutically acceptable carriers. In some embodiments, BMPs are dissolved in a solution containing a particular concentration of finger-1 peptide analogs. In some embodiments, the ratio of concentrations is 1:1, but it may be less or more. Without being bound by any particular theory, it is thought that the finger-1 peptide analog will compete with the first finger regions of the protein, preventing multimerization of monomeric or dimerized BMPs. As a result, it may be desirable to have a higher concentration of peptide than protein, for example, 2:1, 5:1, 10:1, 20:1, or 30:1.

In some embodiments, the concentration of protein to be delivered is in a range of from about 0.01 to about 4 mg per cc or ml of carrier, for example, about 0.05 mg to about 1.5 mg per cc. Exemplary carriers of BMPs include the materials discussed below for therapeutic compositions, hydrogel-forming materials and other polymers and carriers such as those disclosed in U.S. Pat. No. 6,620,406, the contents of which are incorporated herein by reference.

Assays

In another embodiment, finger-1 peptide analogs are used in biologic assays. For example, a finger-1 peptide analog may interact with the BMP receptor and induce a BMP-related biologic response, for example, signal transduction. Assays may also determine responses such as a change in the cell cycle, expression of a particular gene or protein, a visible or measurable alteration in phenotype, a change in the level or modification state of a protein, or other cell characteristics. This response may be measured using commercially available assay or screening test kits. The finger-1 peptide analog may be used to test particular cells to simply determine whether they are responsive to BMP or to identify particular BMPs to which the cell is more or less sensitive. For example, cells may be identified that respond to the finger-1 peptide analogs by modifying a metabolic activity, for example, by increasing or decreasing production of a particular protein, polynucleotide, metabolite, or other cellular component. In an alternative embodiment, the finger-1 peptide analog is employed as a BMP competitor. In this embodiment, the finger-1 peptide analog competes with complete BMP proteins to bind with the cell receptor. For example, cancer cells, bacteria, and other cells involved in disease may be assayed for the presence of particular BMP receptors or other receptors whose binding with finger-1 peptide analogs inhibits a particular function of the cell. Alternatively or in addition, assays may be performed with isolated receptors rather than with cells. In some embodiments, high throughput screening methods using known receptors may be used to assay receptor-peptide interactions.

Exemplary embodiments in which first finger peptide analogs may be employed as BMP agonists include but are not limited to the use of BMP-2 first finger peptide analogs to treat osteoporosis, repair or regenerate bone fractures, and cartilage regeneration, BMP-12 first finger peptide analogs for tendon repair, BMP-9 first finger peptide analogs for induction of cholinergic neuronal differentiation, and GDF-19 first finger peptide analogs for treatment of heart failure. Exemplary embodiments in which first finger peptide analogs may be employed as BMP antagonists include but are not limited to the use of first finger peptide analogs of BMP3 to treat osteoporosis, bone fracture, and bone diseases, BMP15 and GDF9 for contraception, GDF3 to treat type II diabetes, obesity, and metabolic syndrome, BMP4 to repair or regenerate CNS or peripheral nerve tissue, TGF-β to treat various cancers and tumors, or GDF8 to treat muscular dystrophy, sarcopenia, frailty, or neurological disorders. In this embodiment, the first finger peptide fragment competes with the full protein to bind to receptors but then prevents the cellular or tissue response that the protein would otherwise promote.

Peptide binding may be measured or assayed more directly using a radioreceptor assay, in which labeled peptide in the sample competes with unlabeled BMP for binding to the particular cell or receptor, or vice versa. Labeling may be done with $^{125}$I, $^{35}$S, $^{32}$P, or other suitable radioisotopes. As the binding of the finger-1 peptide analog increases, it reduces the amount of BMP that is able to bind. The receptor-BMP complex is then isolated from free ligand, for example by washing (in the case of an adherent cell line), rapid filtration or centrifugation (in the case of a nonadherent cell line or receptor bound to a solid support), or precipitation of the receptor-ligand complex with antibodies, polyethylene glycol, or other precipitating agent followed by filtration or centrifugation (in the case of a soluble receptor). Comparison with a standard curve prepared with known concentrations of labeled ligand allows accurate quantitation of either peptide or protein concentration in the sample. The amount of labeled ligand in the complex is then quantitated, typically by gamma counting, and compared to known standards. These methods have been described in the literature using other receptors (M. Williams, Med. Res. Rev., 11: 147-184 (1991); M. Higuchi and B. B. Aggarwal, Anal Biochem., 204: 53-58 (1992); M. J. Cain, R. K. Garlick and P. M. Sweetman, J. Cardiovasc. Pharm., 17: S150-S151 (1991); each of which are incorporated herein by reference), and are readily adapted to the present system. Other methods of quantifying peptides or BMPs include radioimmunoassay and ELISA, as described in U.S. Pat. No. 4,857,456.

Alternatively or in addition, once a particular finger-1 peptide analog is identified, it may be further optimized by replacing individual amino acids to stabilize a particular secondary structure, prevent the formation interchain cys-cys linkages, or create a better fit with the cell receptor. Such mutations may be identified using computer models or using biological techniques. For example, exemplary methods of protein mutagenesis may be found in Sambrook et al., Molecular Cloning: A Laboratory Manual., 2d ed. (Cold Spring Harbor, N.Y.: Cold Spring Harbor Laboratory Press) (1990). In such an embodiment, it may be desirable to use the peptide or optimized peptide as a therapeutic acting as a BMP mimetic. In other embodiments, individual amino acid residues or peptides may be chemically modified, for example, by glycosylation or derivitization with poly(ethylene glycol).

In another embodiment, the finger-1 peptide analog interacts directly with complete BMP proteins. For example, the finger-1 peptide analog may be used to assay for BMP proteins by preventing homo- or heterodimerization of the protein. In this embodiment, it may be desirable to modify the finger-1 peptide analog so that it can be internalized by a cell, where dimerization often occurs. Alternatively or in addition, the peptide may be employed to positively modulate dimerization of BMP proteins. The interaction of the finger-1 peptide analog and the BMP protein may be assayed using any of the techniques described above. In addition, assays for protein size, for example, native gel electrophoresis, mass spectroscopy, or gel filtration chromatography, may be employed to characterize the effect of the finger-1 peptide analog. In some embodiments, the finger-1 peptide analog may be used as a therapeutic acting as a BMP antagonist by preventing proper BMP function.

In another embodiment, finger-1 peptide analogs may be employed as screens to identify substances, e.g., small molecules, that positively or negatively modulate BMP-BMP or BMP-receptor interactions. Exemplary receptors include but are not limited to serine/threonine kinase receptors, e.g., ACVR1/ALK2, ACVR1B/ALK4, ACVR1C/ALK7, ACVR2/ACTRII, ACVR2B/ACTRIIB, ACVRL1/ALK1, BMPR1A/ALK3, BMPR1B/ALK6, BMPR2/T-ALK, TGFβR1/ALK5, and TGFβR2, and co-receptors such as RGMa, RGMb/DRAGON, RGMc/HFE2, TGFβR3, Cripto, Cryptic, and Endoglin. For example, high throughput assays may be employed to identify a small molecule inhibitor of a BMP. A cell-free assay could be conducted similar to a FRET assay in which the screen detects disruption of the BMP-peptide interaction. For example, either the BMP or the finger-1 peptide analog may be modified with a donor molecule, while the other is modified with an acceptor molecule.

In another embodiment, finger-1 peptide analogs may be modified to be constrained in a particular configuration to retain a given secondary structure. For example, particular amino acids in the finger-1 peptide analog may be replaced with cysteines that will form disulfide bonds and stabilize a particular conformation. Alternatively or in addition, cysteines may be added to the N- and C-terminal ends of the finger-1 peptide analog to constrain the peptide or stabilize a particular conformation. In some embodiments, it may be desirable to unfold wild type or mutant finger-1 peptide analogs and allow them to refold in an alternative configuration. For example, the finger-1 peptide analog may be solubilized and denatured using a chaotropic agent. Separation of the finger-1 peptide analog from the chaotropic agent allows it to refold in a thermodynamically favored configuration. When cysteine residues are present in the primary amino acid sequence of the protein, it may be desired to accomplish the refolding in an environment which allows correct formation of disulfide bonds (e.g., a redox system). General methods of refolding are disclosed in Kohno, Meth. Enzym., 185:187-195 (1990). Chaperonins may also be employed to mediate folding.

Therapeutic Compositions

Finger-1 peptide analogs identified as having therapeutic potential may be applied to tissue in the form of a buffer solution. An exemplary buffer solution is a composition comprising, in addition to the peptide, about 1.0 to about 10.0% (w/v) glycine, about 0.1 to about 5.0% (w/v) of a sugar, e.g., sucrose, about 1 to about 20 mM glutamic acid hydrochloride, and optionally about 0.01 to about 0.1% of a non-ionic surfactant, such as polysorbate 80 or Tween. Exemplary solutions are from about 1% to about 20% w/v cellulosic carrier/buffer. If desired, a salt may be added.

More viscous materials may also be used as carriers. Such materials may be include pharmaceutically acceptable materials having viscosity and polarity such that, when combined with the finger-1 peptide analog, form a composition that possesses appropriate handling characteristics for the tissue site. For example, it may be desirable to have relatively less viscous (but still not runny) material for use in a periodontal site than at a bone fracture. Adding the carrier to the peptide allows the finger-1 peptide analog to remain in the disease or lesion site for a time sufficient to allow the finger-1 peptide analog to act on local cells by either upregulating or downregulating various metabolic activities. The carrier may also allow the finger-1 peptide analog to be released from the lesion, defect or disease site over a time interval.

An exemplary family of carriers for administration of the peptides are porous particulate polymers, described in detail in U.S. Pat. No. 5,171,579, the entire disclosure of which is incorporated herein by reference. An alternative carrier useful for the present invention is a formulation of osteogenic protein, porous particulate polymers and another sequestering or carrier agent, such as cellulosic material. Other materials that may be employed as carriers or sequestering agents include carboxymethylcellulose, hyaluronic acid, sodium alginate, poly(ethylene glycol), polyoxyethylene oxide, carboxyvinyl polymer and poly(vinyl alcohol). These compositions are described in the published PCT application WO 93/00050, the entire disclosure of which is hereby incorporated herein by reference. The sequestering agent may be present in a concentration of about 1 to about 10% (w/v implant). Where porous particulate particulate polymers are employed as the carrier, porous particulate polymer/cellulosic sequestering agent may optionally be further combined with aqueous glycerol as a diluent, for example, in concentrations of about 10 to about 80% (v/v) with exemplary ratios of sequestering agent/liquid solution:porous particulate polymers from about 0.1 to about 0.9 (v/v).

Another exemplary family of carriers is collagenous materials. Suitable collagen materials include Collastat™ and Helistat™ collagen sponges (Integra LifeSciences Corp., Plainsboro, N.J.). Other collagen materials which may be suitable for use in the present invention are described in U.S. Pat. No. 5,206,028; U.S. Pat. No. 5,024,841; U.S. Pat. No. 5,256,418. A collagen carrier is may be in the form of a sponge. The collagen sponge may be loaded with peptide prior to administration by soaking the sponge in the desired volume and concentration of peptide for a suitable time period. The collagen sponge may soak loaded with peptide in a range from about 10% to about 150% v/v [ml protein/cc dry sponge], for example, about 10 to about 60% v/v. Alternatively, the peptide may be adsorbed to the collagen sponge during production. In this case, peptide may be added to the collagen sponge during production and lyophilized to form a unitary product. The peptide may be added in a ratio of from about 10 to about 150% v/v, for example, in a range from about 60 to about 80% v/v.

Another exemplary family of carriers is cellulose-based materials such as alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, for example, the cationic salts of carboxymethylcellulose (CMC). The crosslink and molecular weight of these materials and any other polymer carrier described herein may be modified to adjust the delivery rate of the encapsulated peptide and to stabilize the peptide in vivo.

In the case of cellulosic carriers, the carrier may be in the form of a hydrated cellulosic viscous gel. Viscosity of cellulosic materials may be increased through mechanical means, such as high agitation for a suitable period of time, followed by autoclaving. The peptide and cellulosic carrier may be in a solution of suitable buffer. An exemplary buffer solution is a composition comprising about 1.0 to about 10.0% (w/v) glycine, about 0.1 to about 5.0% (w/v) of a sugar, preferably sucrose, about 1 to about 20 mM glutamic acid hydrochloride, and optionally about 0.01 to about 0.1% of a non-ionic surfactant, such as polysorbate 80. Exemplary solutions are from about 1% to about 20% w/v cellulosic carrier/buffer. If desired, a salt may be added. The amount of peptide combined with a viscous gel carrier may be in a range of from about 0.05 to about 1.5 mg, for example, from about 0.1 to about 1.0 mg per cubic centimeter of implant material required.

Other materials which may be suitable for use as carriers for finger-1 peptide analogs according to various embodiments include but are not limited to demineralized bone, polyglyconate, hyaluronic acid, surgical mesh or sutures, temperature-sensitive polymers, and minerals and ceramics, such as calcium phosphates, hydroxyapatite, etc, and combinations of these. Other potential carriers include carriers for injectable formulations of BMPs. Suitable carriers for injectable formulations include, for example, soluble collagen, hyaluronic acid, polylactic acid/polyethylene glycol, and polymers.

Finger-1 peptide analogs for use in this embodiment may simply be combined with the carrier and complete protein or may be immobilized on the carrier. For example, amine-terminated peptides may be attached to carboxylated carriers using standard polymer chemistry techniques. In another example, peptides may be terminated with carboxy-NHS and attached to aminated polymers. Alternatively or in addition, peptides may be biotinylated and coordinated with carriers that have been functionalized with streptavidin.

Alternative carriers for finger-1 peptide analogs include micelles. For example, double emulsion techniques such as those described in Gref, et al, *Science,* 1994, 263:1600-1603 may be used to encapsulate therapeutic compositions in micelles that may then be administered to a subject using any of the techniques described herein or any other delivery techniques known to those of skill in the art. In some embodiments, the micelle surface may include a targeting agent. The targeting agent may be covalently attached to the micelle or may be retained using ligand-receptor interactions (e.g., biotin-streptavidin) or electrostatic interactions. Exemplary targeting agents include antibodies and antibody fragments, nucleic acid ligands (e.g., aptamers), oligonucleotides, oligopeptides, polysaccharides, low-density lipoproteins (LDLs), folate, transferrin, asialycoproteins, gp120 envelope protein of the human immunodeficiency virus (HIV), carbohydrates, polysaccharides, enzymatic receptor ligands, sialic acid, glycoprotein, lipid, small molecule, bioactive agent, biomolecule, immunoreactive fragments such as the Fab, Fab', or $F(ab')_2$ fragments, etc.

Peptides for use as a therapeutic may be modified to increase their in vivo stability, increasing their circulation time and reducing the rate of elimination from the body. For example, peptides may be functionalized or combined with with a poly(alkylene glycol) chain such as poly(ethylene glycol) (PEG) or poly(propylene glycol) (PPG). The optimal molecular weight of such polymer chains may be optimized using techniques known to those of skill in the art. Alternatively or in addition, peptides may be conjugated with sialyl groups or polysialyl chains. Peptides may also be modified by chemically modifying amino acid residues with smaller chemical groups such as methyl, sulfate, etc. Individual amino acid residues may also be replaced with non-natural amino acids such as D-stereoisomers or beta-residues. In some embodiments, peptides may be stabilized by inter- or intra-chain covalent or non-covalent links. These links may be promoted by adding appropriate amino acid residues to the peptide or by modifying amino acids in the peptide with appropriate chemical groups, such as thiol, hydrogen bond donors and acceptors, etc. Peptides may also be associated with or fused (e.g., at the N- or C-terminals or internally) with the full length or a fragment of a natural or synthetic protein that acts as a presentation enhancer. Exemplary proteins are known to those of skill in the art and include bovine serum albumin.

The finger-1 peptide analogs, in a suitable buffer or combined with a suitable carrier such as those described above, may be applied directly to a tissue and/or to a site in need of tissue repair. For example, the peptide may be physically applied to the tissue through spraying or dipping, or using a brush or other suitable applicator, such as a syringe for injection. Alternatively, or in addition, the peptide may be directly applied to the site in need of tissue repair.

In some embodiments, therapeutic compositions according to an embodiment of the invention may be administered to a subject or may first be formulated for delivery by any available route including, but not limited to parenteral (e.g., intravenous), intradermal, subcutaneous, oral, nasal, bronchial, opthalmic, transdermal (topical), transmucosal, rectal, and vaginal routes. Inventive pharmaceutical compositions may include a purified polypeptide or protein expressed from a mammalian cell line and a delivery agent (i.e., a cationic polymer, peptide molecular transporter, surfactant, etc., as described above) in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Solutions or suspensions used for parenteral, intradermal, or subcutaneous application may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use often include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Exemplary pharmaceutical formulations are stable under the conditions of manufacture and storage and are preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the purified polypeptide or protein in the required amount in an appropriate solvent with one or a combination of ingredients enumerated above, as required, followed by filtered sterilization. Generally, dispersions are prepared by incorporating the purified polypeptide or protein expressed from a mammalian cell line into a sterile vehicle which contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof.

Oral compositions may include an inert diluent or an edible carrier. For the purpose of oral therapeutic administration, the purified polypeptide or protein can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions comprising a purified polypeptide or protein expressed from a mammalian cell line and a delivery agent are preferably delivered in the form of an aerosol spray from a pressured container or dispenser which contains a suitable propellant, e.g., a gas such as carbon dioxide, or a nebulizer. The present invention contemplates delivery of the compositions using a nasal spray, inhaler, or other direct delivery to the upper and/or lower airway. Intranasal administration of DNA vaccines directed against influenza viruses has been shown to induce CD8 T cell responses, indicating that at least some cells in the respiratory tract can take up DNA when delivered by this route, and the delivery agents of the invention will enhance cellular uptake. According to certain embodiments of the invention the compositions comprising a purified polypeptide expressed from a mammalian cell line and a delivery agent are formulated as large porous particles for aerosol administration. The transepithelial absorption of compositions according to an embodiment of the invention may be enhanced using the techniques disclosed in U.S. Patent Publication No. 20030235536, the contents of which are incorporated herein by reference.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified polypeptide or protein and delivery agents are formulated into ointments, salves, gels, or creams as generally known in the art.

The compositions can also be prepared in the form of suppositories (e.g., with conventional suppository bases such as cocoa butter and other glycerides) or retention enemas for rectal delivery.

In one embodiment, the compositions are combined with an agent that will protect the polypeptide or protein against rapid elimination from the body, such as a controlled release formulation, including implants and microencapsulated delivery systems. The agent may also serve as a carrier for the composition. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active polypeptide or protein calculated to produce the desired therapeutic effect in association with the required pharmaceutical carrier.

The polypeptide or protein according to an embodiment of the invention can be administered at various intervals and over different periods of time as required. The skilled artisan will appreciate that certain factors can influence the dosage and timing required to effectively treat a subject, including but not limited to the severity of a disease or disorder, previous treatments, the general health and/or age of the subject, and other diseases present. Generally, treatment of a subject with a polypeptide or protein as described herein can include a single treatment or, in many cases, can include a series of treatments. It is furthermore understood that appropriate doses may depend upon the potency of the polypeptide or protein and may optionally be tailored to the particular recipient, for example, through administration of increasing doses until a preselected desired response is achieved. It is understood that the specific dose level for any particular animal subject may depend upon a variety of factors including the activity of the specific polypeptide or protein employed, the age, body weight, general health, gender, and diet of the subject, the time of administration, the route of administration, the rate of excretion, any drug combination, and the degree of expression or activity to be modulated.

The present invention includes the use of inventive compositions for treatment of nonhuman animals. Accordingly, doses and methods of administration may be selected in accordance with known principles of veterinary pharmacology and medicine. Guidance may be found, for example, in Adams, R. (ed.), *Veterinary Pharmacology and Therapeutics*, 8th edition, Iowa State University Press; ISBN: 0813817439; 2001.

Inventive pharmaceutical compositions can be included in a container, pack, or dispenser together with instructions for administration.

EXAMPLES

Example 1

BMP-12 was immobilized on NHS-activated Sepharose™ beads at a ratio of about 20 mg:4 mL and the resulting media combined with water or neutral saline buffer to prepare a column. CHO-conditioned media augmented with 1.2 M NaCl was loaded onto the column. In some cases, the media was preconcentrated with respect to BMP before loading. The column was washed with 15 CV (column volumes) of 1.2 M NaCl in 40 mM $Na_2HPO_4$ at pH 7.2, followed by 0.5 M arginine/0.5 M NaCl in 20 mM Tris at pH 7.5 (15 CV) and a low salt wash (50 mM ammonium acetate at pH 7, 15 CV). The column was further eluted with acetic acid, using a 5 CV gradient to 50 mM acetic acid at pH 3, followed by a 15 CV chase. Finally, the column was eluted with 5CV of the acetic acid solution with 6M guanidine hydrochloride (GuHCl).

Figure 3:
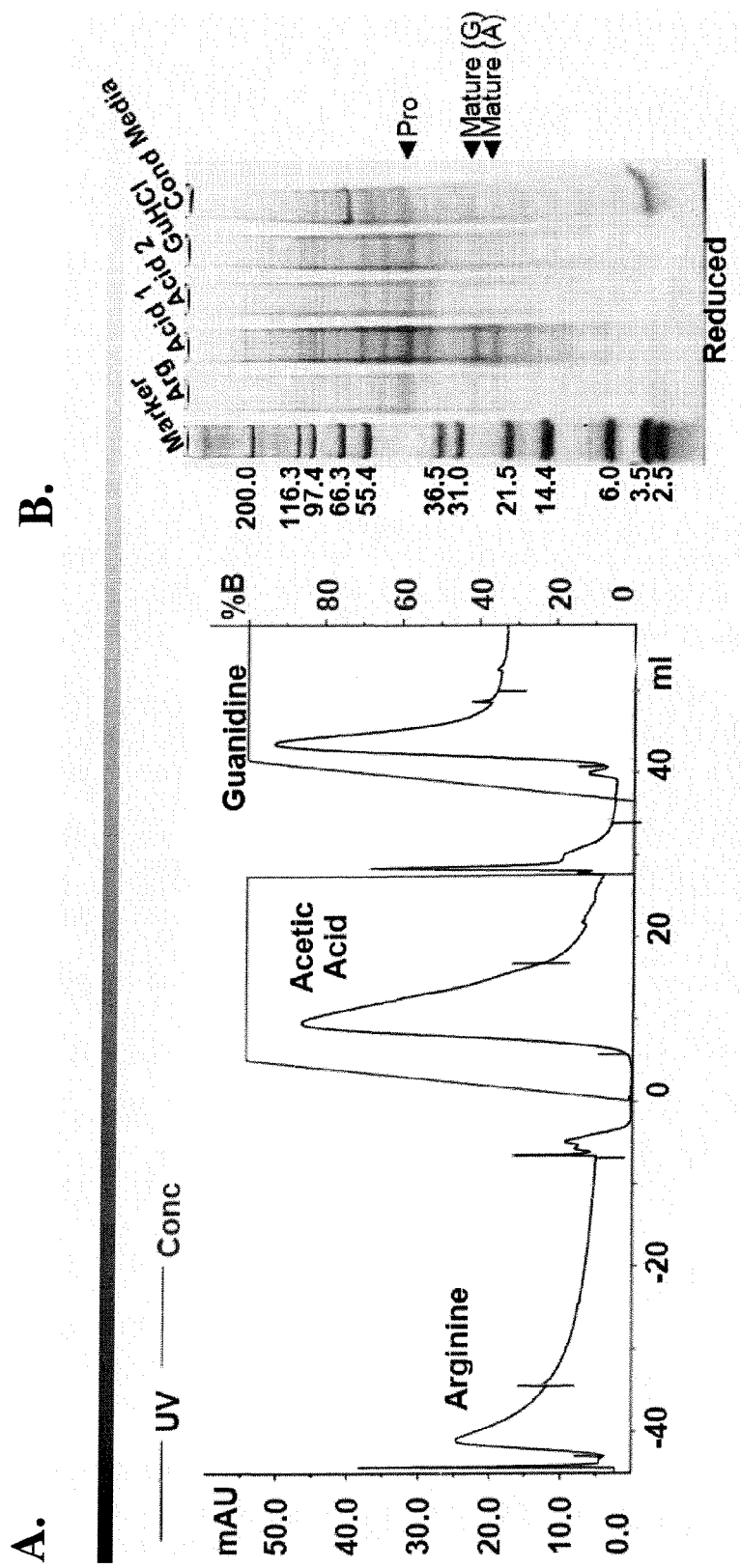
FIG. 3 is a chromatogram (A) and a photograph of an SEC gel (B) showing the elution of BMP-3 from a column employing immobilized BMP-12.

BMP-3 was effectively captured by the chromatography media and eluted with acetic acid (FIG. 3A). The eluate was analyzed using HPLC. As seen in FIG. 3B, a propeptide fragment copurifies along with the mature protein, and trace amounts of the mature BMP-3 were also observed in the guanidine peak.

Example 2

Figure 4:
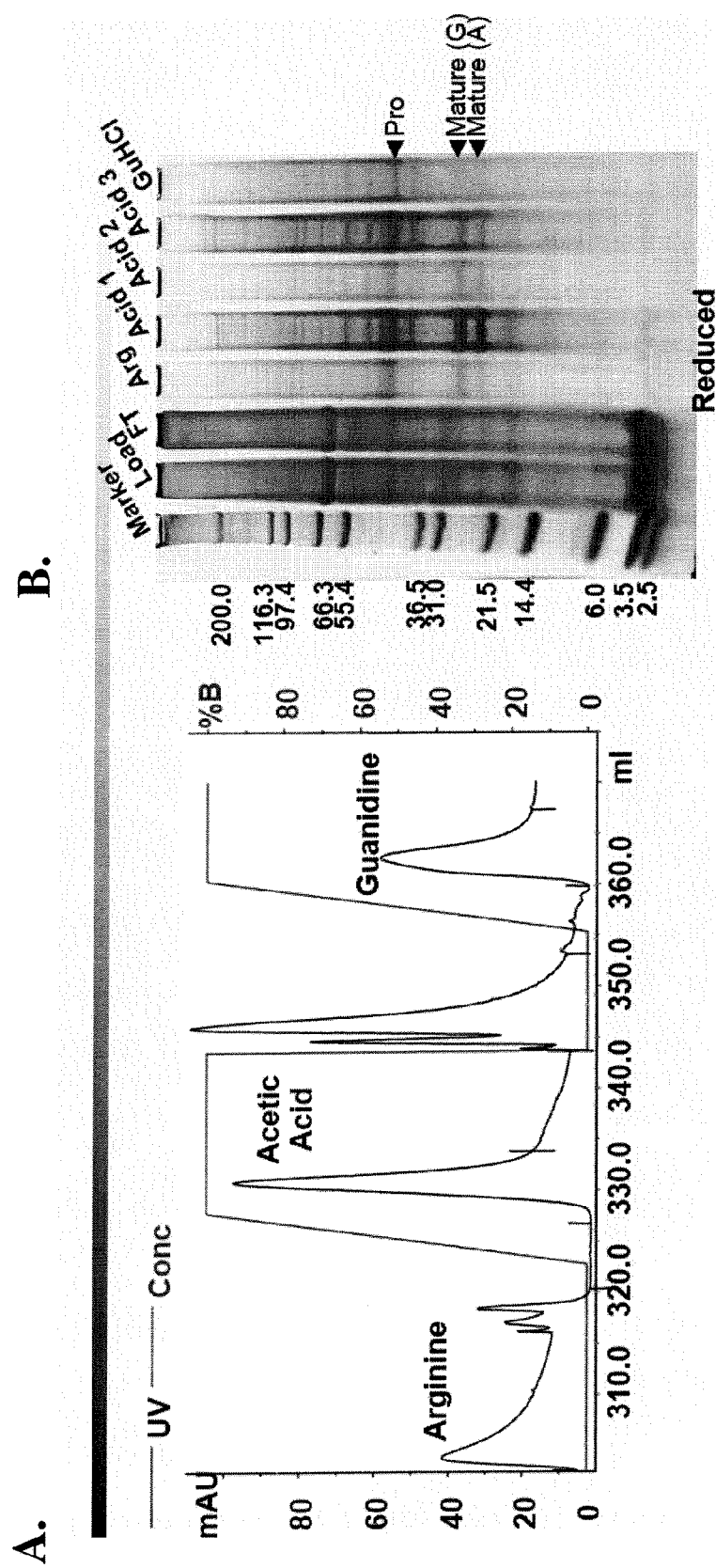
FIG. 4 is a chromatogram (A) and a photograph of an SEC gel (B) showing the elution of BMP-3 from a column employing immobilized BMP-2.

BMP-2 was immobilized on sepharose beads as in Example 1 and used to test the loading and elution of BMP-3. As shown in FIG. 4, BMP-3 was effectively captured by the high ionic strength solution and was eluted with acetic acid. As for the BMP-12 column, a propeptide fragment copurifies along with the mature protein, and trace amounts of the mature BMP-3 were also observed in the guanidine peak.

Example 3

Figure 5:
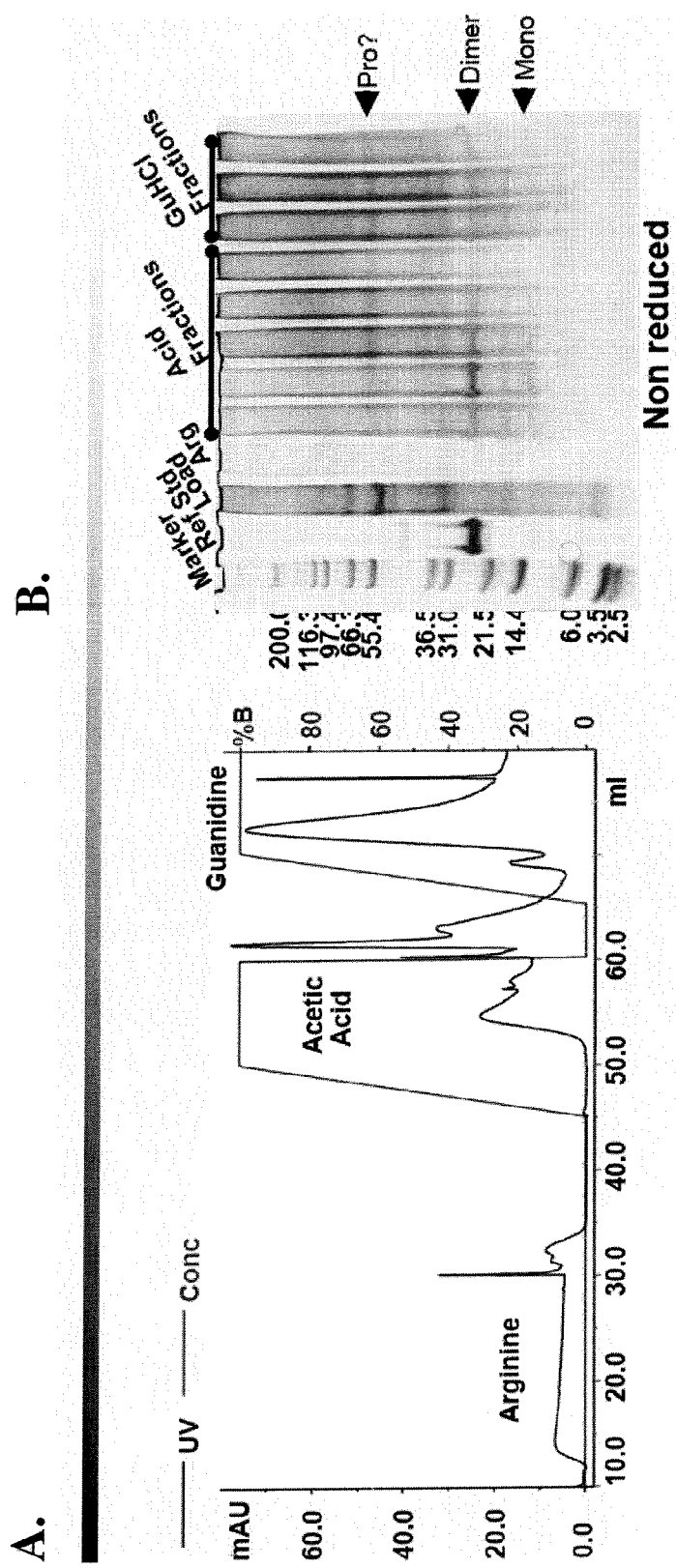
FIG. 5 is a chromatogram (A) and a photograph of an SEC gel (B) showing the elution of BMP-12 from a column employing immobilized BMP-12.

BMP-12 was loaded and eluted from a BMP-12 affinity column as in Example 1. The BMP-12 was effectively captured by the column using the high salt solution and eluted with acetic acid and guanidine (FIG. 5). Both the monomeric and dimeric forms of BMP-12 were captured.

Example 4

Figure 6:
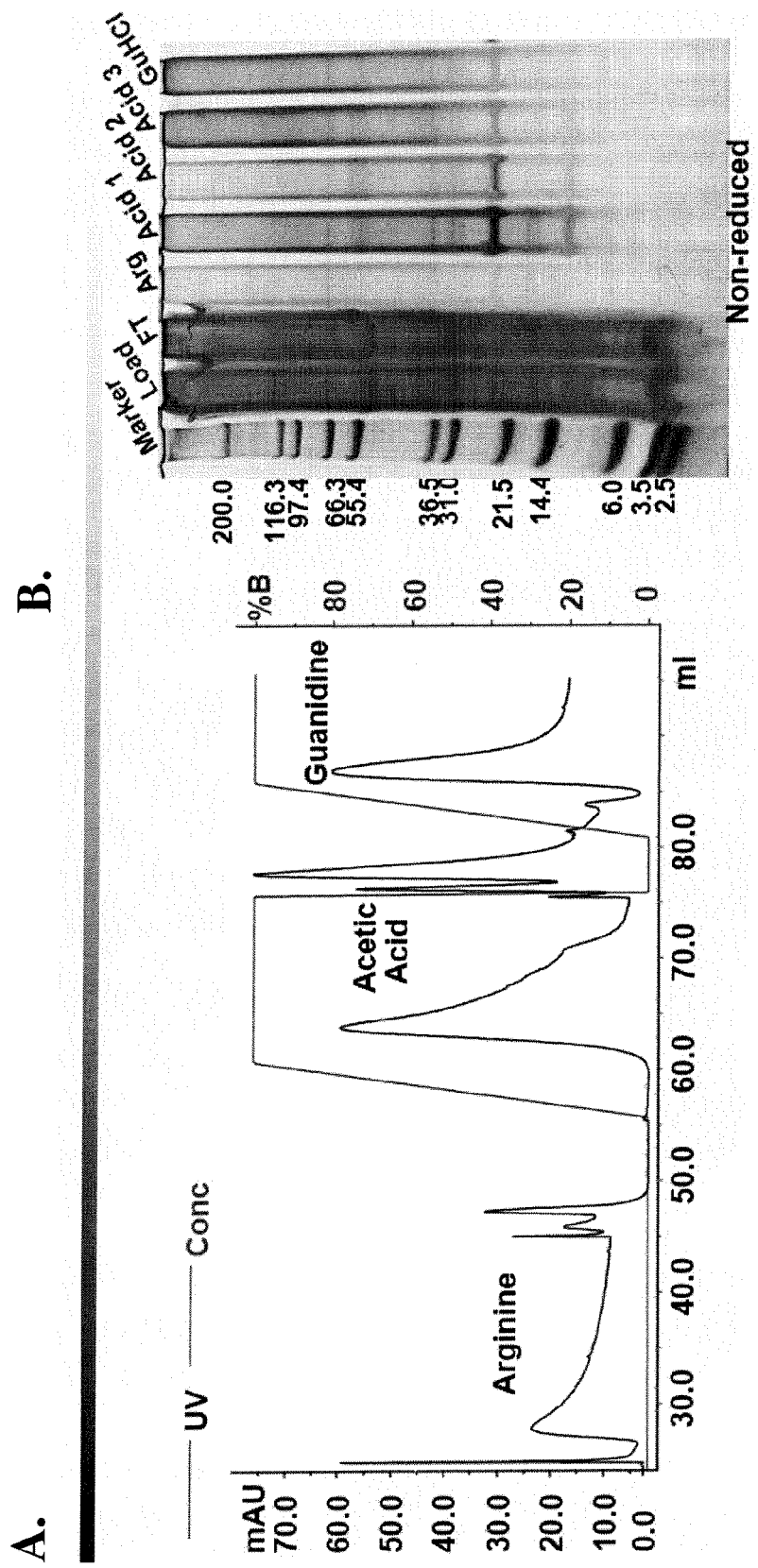
FIG. 6 is a chromatogram (A) and a photograph of an SEC gel (B) showing the elution of BMP-12 from a column employing immobilized BMP-2.

BMP-12 was loaded and eluted from a BMP2 affinity column as in Examples 1 and 2. The BMP-12 was effectively captured by the column using the high ionic strength solution and was eluted with acetic acid and guanidine (FIG. 6).

Example 5

Figure 7:
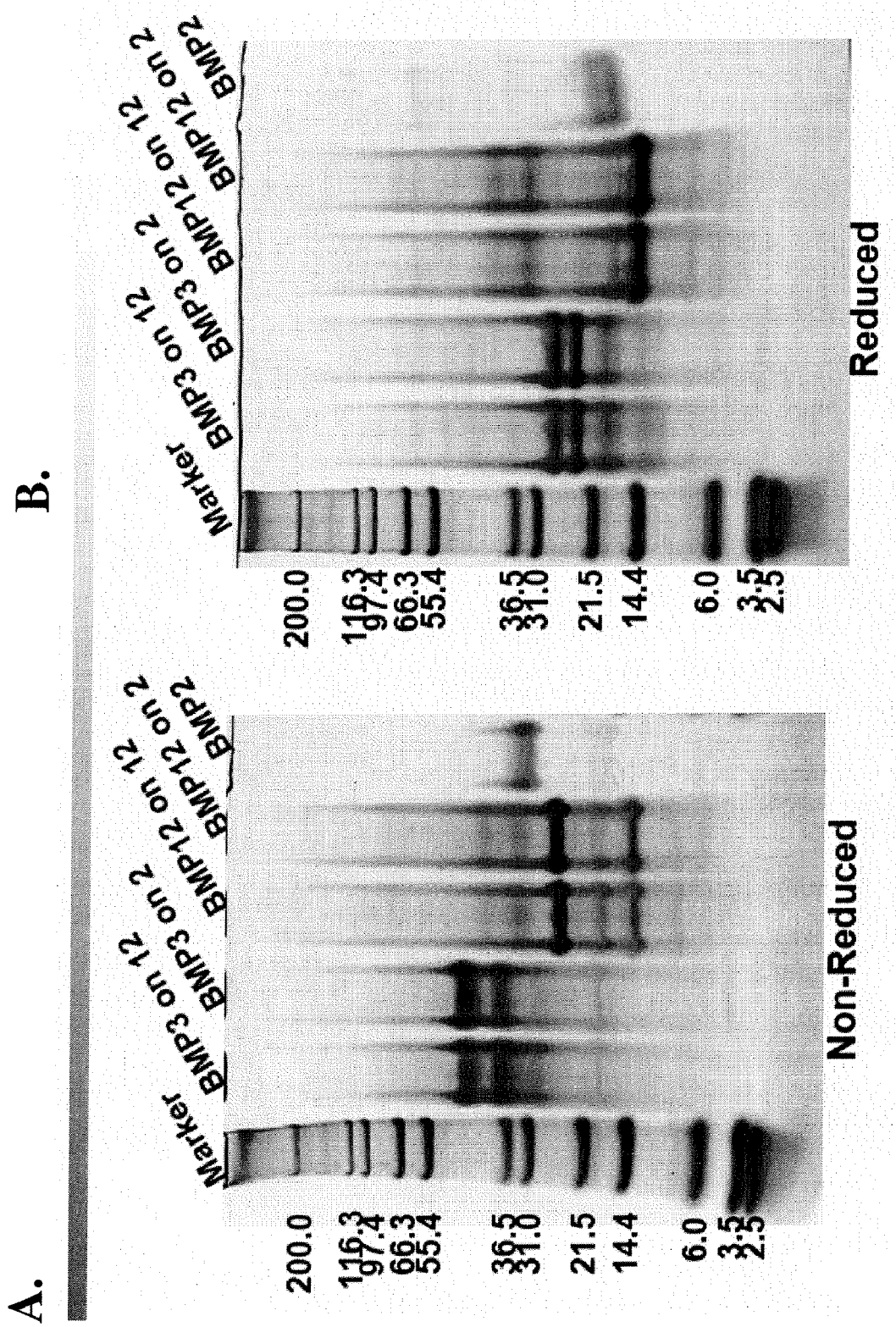
FIG. 7 is a set of photographs of SEC gels (A: non-reduced, B: reduced) showing the elution of various BMPs from reversed phase HPLC column employing immobilized BMPs.

The BMP affinity resins using BMP-12 and BMP-2 were prepared as described in Examples 1 and 2 and used to prepare HPLC columns. These columns were used loaded with BMP-3 and BMP-12. As shown in FIG. 7, BMP-12 and BMP-2 were equally effective as affinity ligands for reverse phase HPLC. In some cases, size exclusion or reverse phase chromatography techniques were employed to enhance purification.

Example 6

Figure 8:
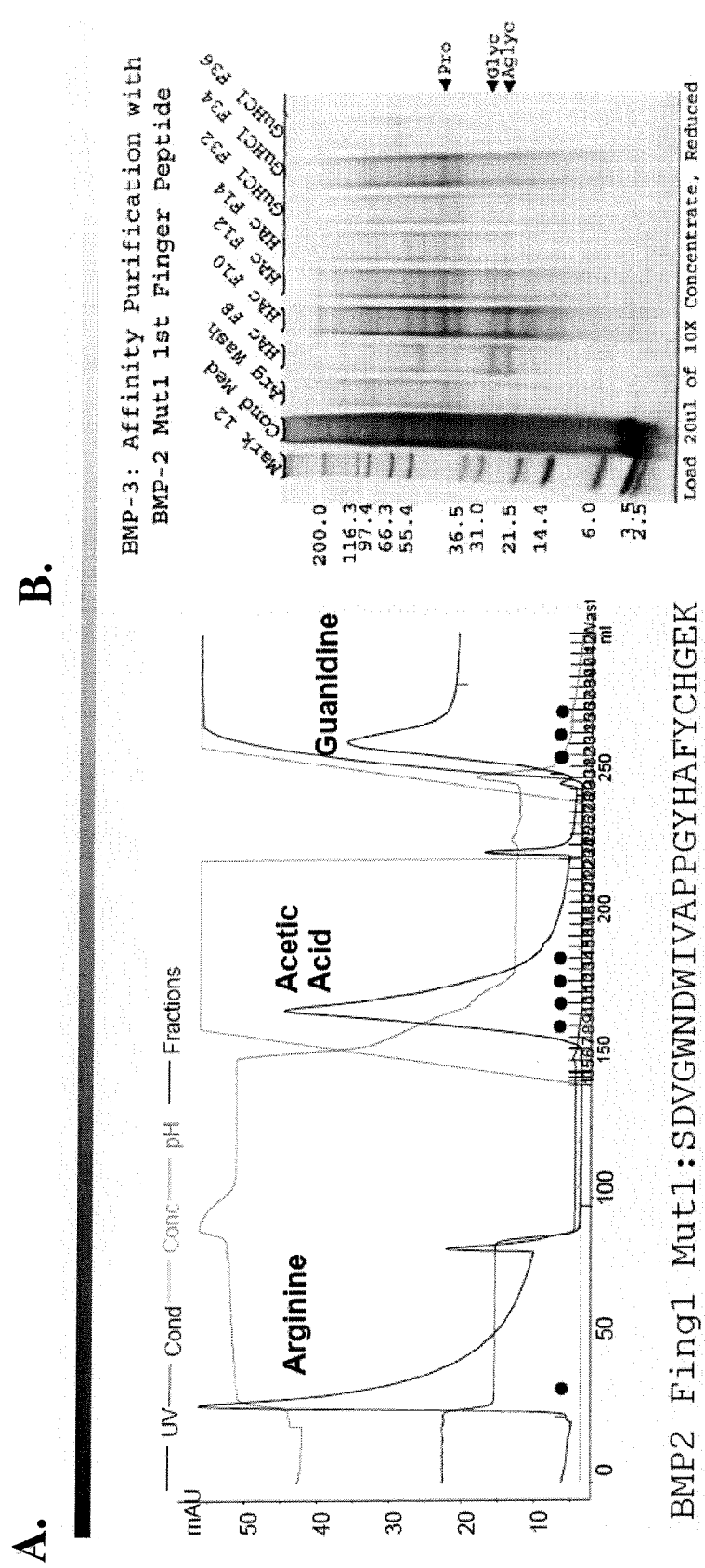
FIG. 8 is a chromatogram (A) and a photograph of an SEC gel (B) showing the elution of BMP-3 from a column employing immobilized BMP-2 mutant fragments.

A mutant of the BMP-2 finger 1 peptide (SDVGWNDWIVAPPGYHAFYCHGE<u>K</u>) (SEQ ID NO: 1) was linked to sepharose beads via a C-terminal lysine at a ratio of 5 mg peptide/mL resin. 4 mL of the resulting resin (1.6×2.0 cm) was used to prepare a column. The column was loaded with BMP-3 and eluted as in Example 1. As shown in FIG. 8, the BMP-3 was effectively captured by the column using the high salt solution and eluted, along with a propeptide fragment, in acetic acid. In general, chromatography with the immobilized peptides provided higher purity product than with the whole protein.

Example 7

Figure 9:
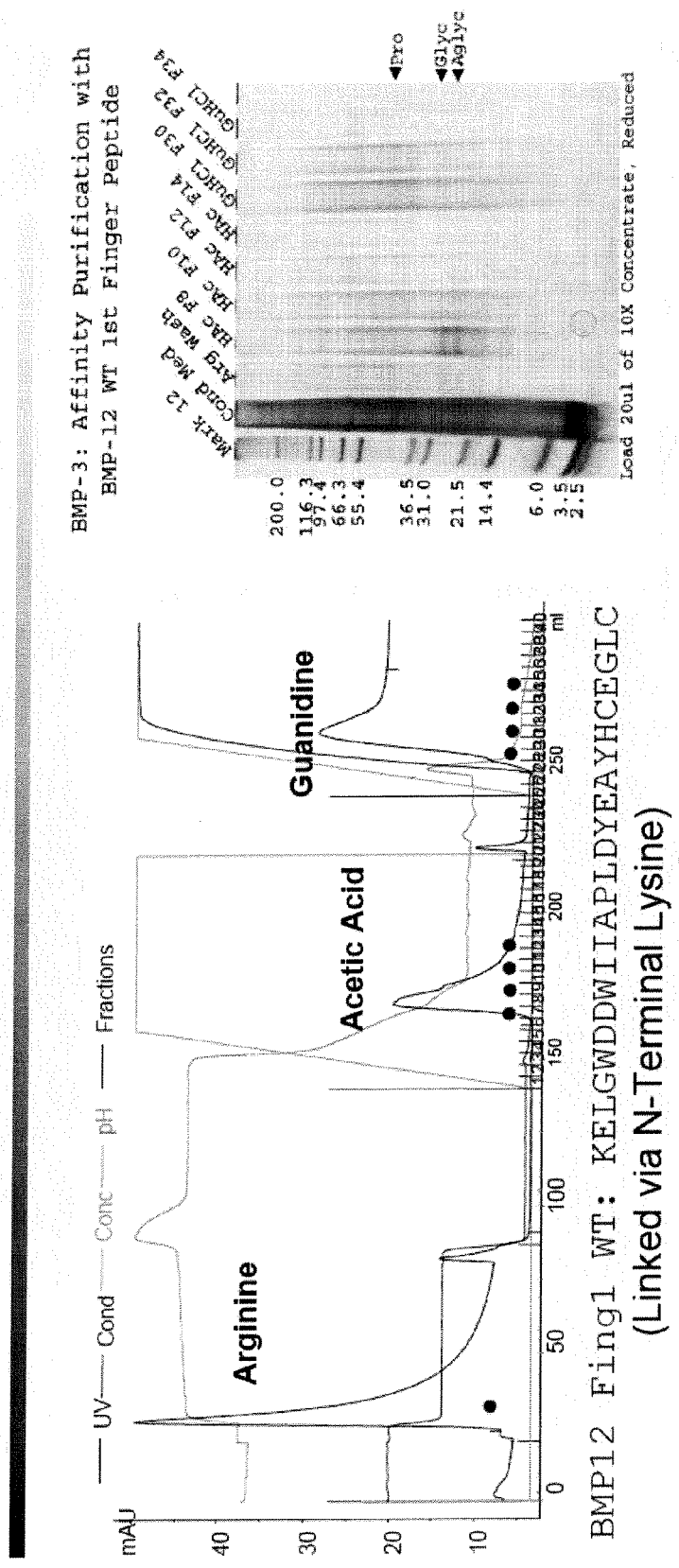
FIG. 9 is a chromatogram (A) and a photograph of an SEC gel (B) showing the elution of BMP-3 from a column employing immobilized BMP-12 wild-type fragment.

A wild-type BMP-12 finger 1 peptide (KELGWDDWIIAPLDYEAYHCEGLC) (SEQ ID NO: 2) was used to purify BMP-3 as in Example 1. As shown in FIG. 9, the BMP-3 was effectively captured by the column using the high salt solution and eluted in acetic acid. Less of the propeptide fragment eluted than in Example 6. In general, the immobilized BMP-12 was less effective than the BMP-2 mutant. SDS-PAGE shows that the immobilized BMP-12 peptide oligomerized, perhaps due to the free cysteine residues.

Example 8

Figure 10:
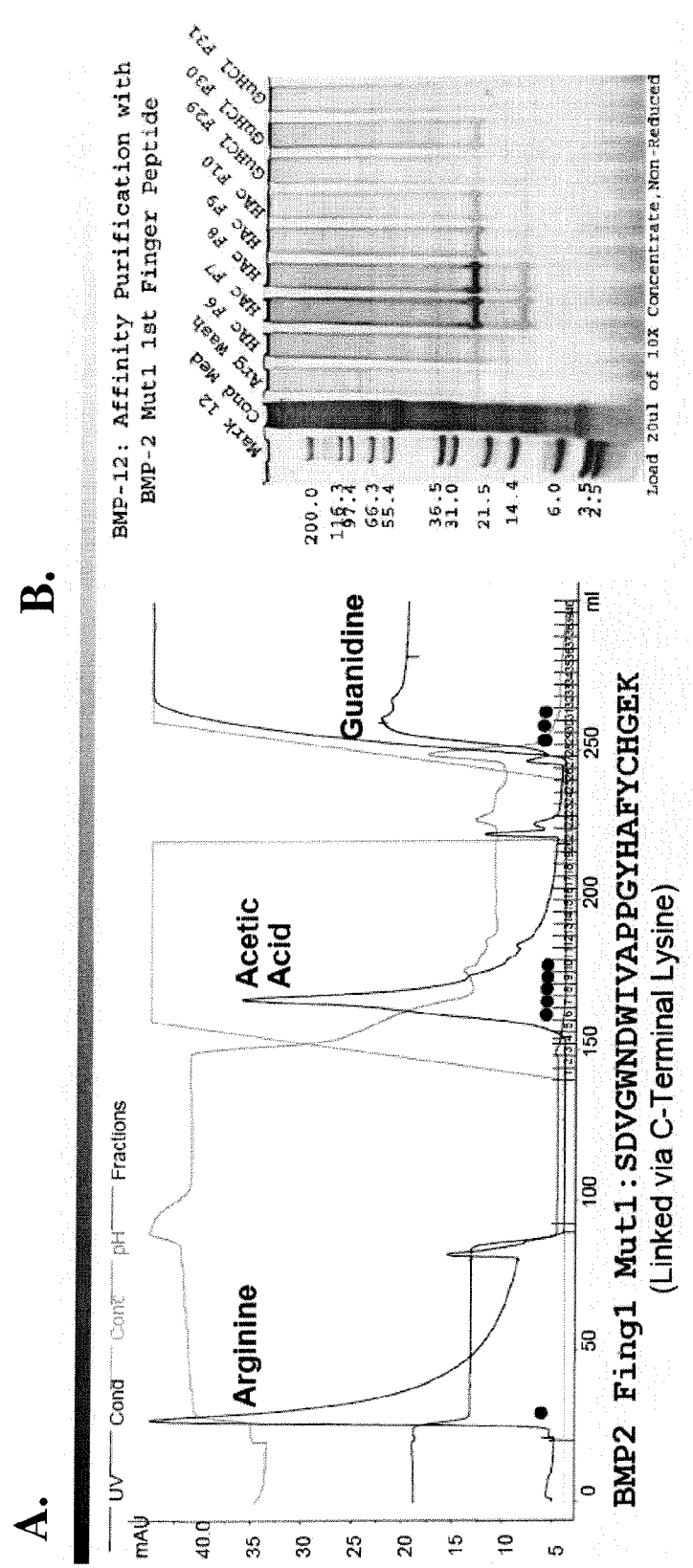
FIG. 10 is a chromatogram (A) and a photograph of an SEC gel (B) showing the elution of BMP-12 from a column employing immobilized BMP-2 mutant fragments.

BMP-12 was purified using a column prepared with the BMP-2 mutant peptide described in Example 6. As shown in FIG. 10, the BMP-12 was effectively captured by the column using the high salt solution and eluted with acetic acid. A small amount of BMP-12 eluted with 6M GuHCl.

Example 9

Figure 11:
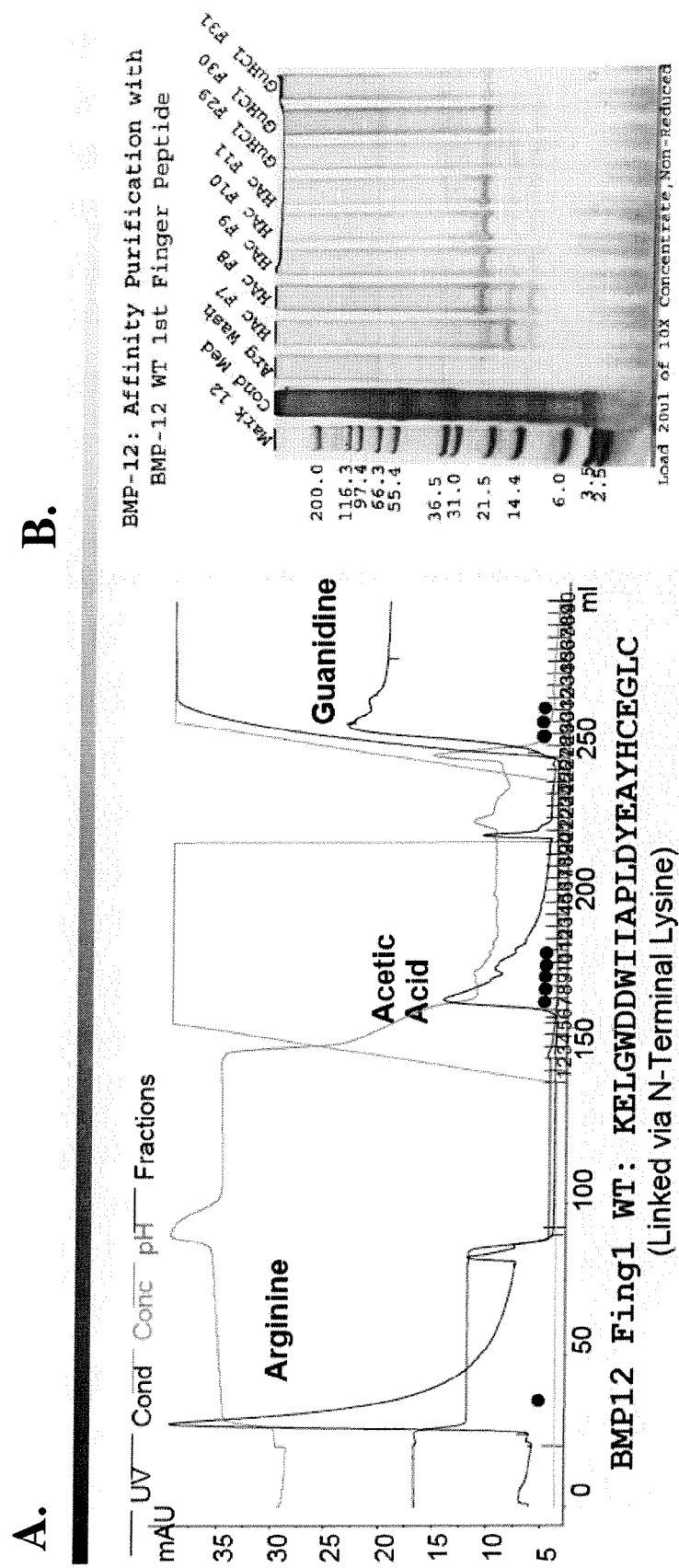
FIG. 11 is a chromatogram (A) and a photograph of an SEC gel (B) showing the elution of BMP-12 from a column employing immobilized BMP-2 mutant fragments.

BMP-12 was purified using a column prepared with the BMP-12 wild type peptide described in Example 7. As shown in FIG. 11, the BMP-12 was effectively captured by the column using the high ionic strength solution and eluted with acetic acid. A small amount of BMP-12 eluted with 6M GuHCl.

Example 10

Figure 12:
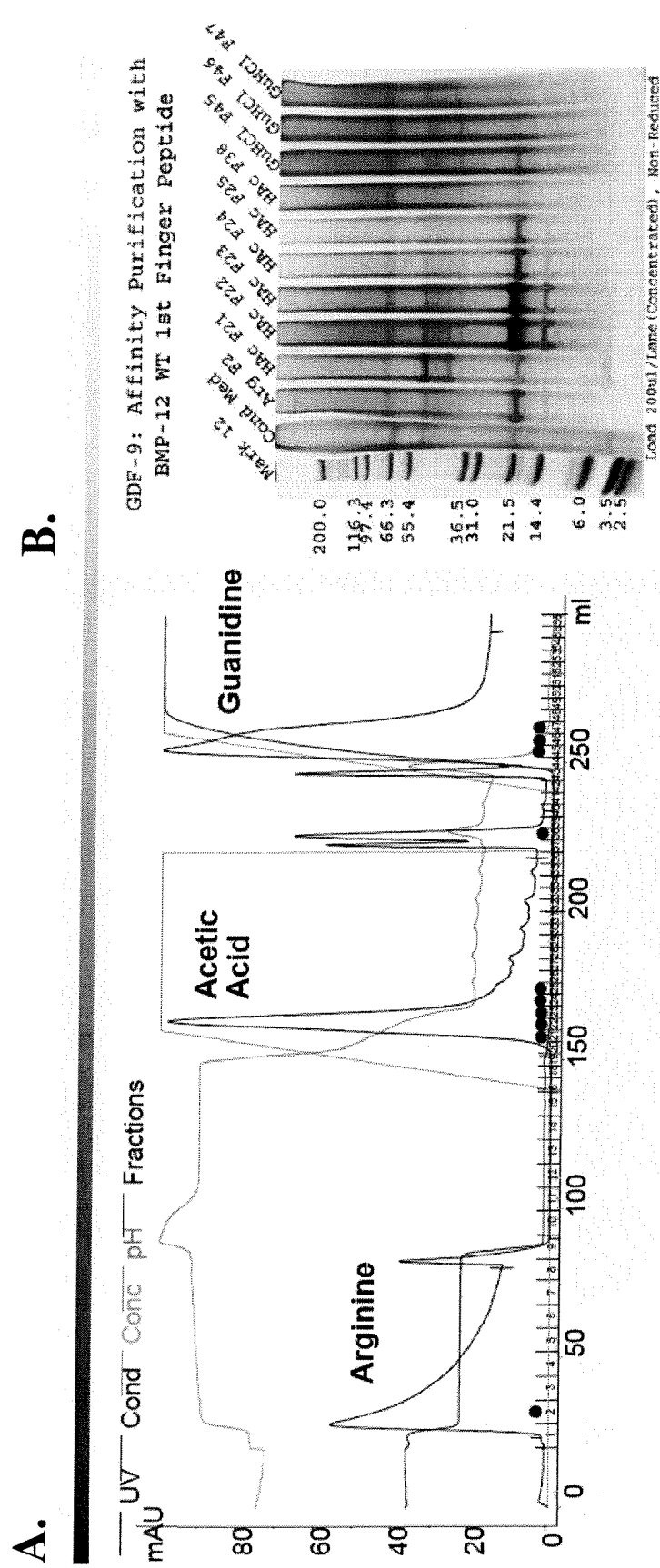
FIG. 12 is a chromatogram (A) and a photograph of an SEC gel (B) showing the elution of GDF-9 from a column employing immobilized BMP-2 mutant fragments.

GDF-9 was purified using a column prepared with the BMP-2 first finger mutant peptide described in Example 6. As shown in FIG. 12, the GDF-9 was effectively captured by the column using a high salt solution and eluted with both 500 mM arginine and acetic acid. A lower molecular weight contaminant was also present.

Example 11

Put in Prophetic Examples for Remaining Peptide Mutants

BMP affinity resins are prepared using one or more of the following peptides:

TABLE 1

Exemplary Peptide Sequences for Preparation of Affinity Resins

```
BMP2    Fing1   WT:     SDVGWNDWIVAPPGYHAFYCHGEC  (SEQ ID NO: 3)
BMP2    Fing1   Mut1:   SDVGWNDWIVAPPGYHAFYCHGEK  (SEQ ID NO: 1)
BMP2    Fing1   Mut2:   SDVGANDWIVAPPGYHAFYCHGEC  (SEQ ID NO: 4)
BMP2    Fing1   Mut3:   SDVGANDWIVAPPGYHAFYCHGEK  (SEQ ID NO: 5)
BMP2    Fing1   Mut4:   SDVGWNDWIVAPPGYHAFYCHAEC  (SEQ ID NO: 6)
BMP2    Fing1   Mut5:   SDVGWNDWIVAPPGYHAFYCHAEK  (SEQ ID NO: 7)
BMP2    Fing1   Mut6:   SDVGANDWIVAPPGYHGFYCHGEC  (SEQ ID NO: 8)
BMP2    Fing1   Mut7:   SDVGANDWIVAPPGYHGFYCHGEK  (SEQ ID NO: 9)
BMP2    Fing1   WT:     LYVDFSDVGWNDWIVAPPGYHAFY  (SEQ ID NO: 10)
BMP2    Fing1   Mut1:   LYVDFSDVGANDWIVAPPGYHAFY  (SEQ ID NO: 11)
BMP2    Fing1   Mut2:   LYVDFSDVGWNDWIVAPPGYHGFY  (SEQ ID NO: 12)
BMP12   Fing1   WT:     KELGWDDWIIAPLDYEAYHCEGLC  (SEQ ID NO: 2)
BMP12   Fing1   Mut1:   KELGWDDWIIAPLDYEAYHCEGLK  (SEQ ID NO: 13)
BMP12   Fing1   Mut2:   AELGWDDWIIAPLDYEAYHCEGLK  (SEQ ID NO: 14)
BMP3    Fing1   WT:     ADIGWSEWIISPKSFDAYYCSGAC  (SEQ ID NO: 15)
BMP3            Mut1:   ADIGWSEWIISPKSFDAYYCSGAK  (SEQ ID NO: 16)
```

Example 12

Figure 13:
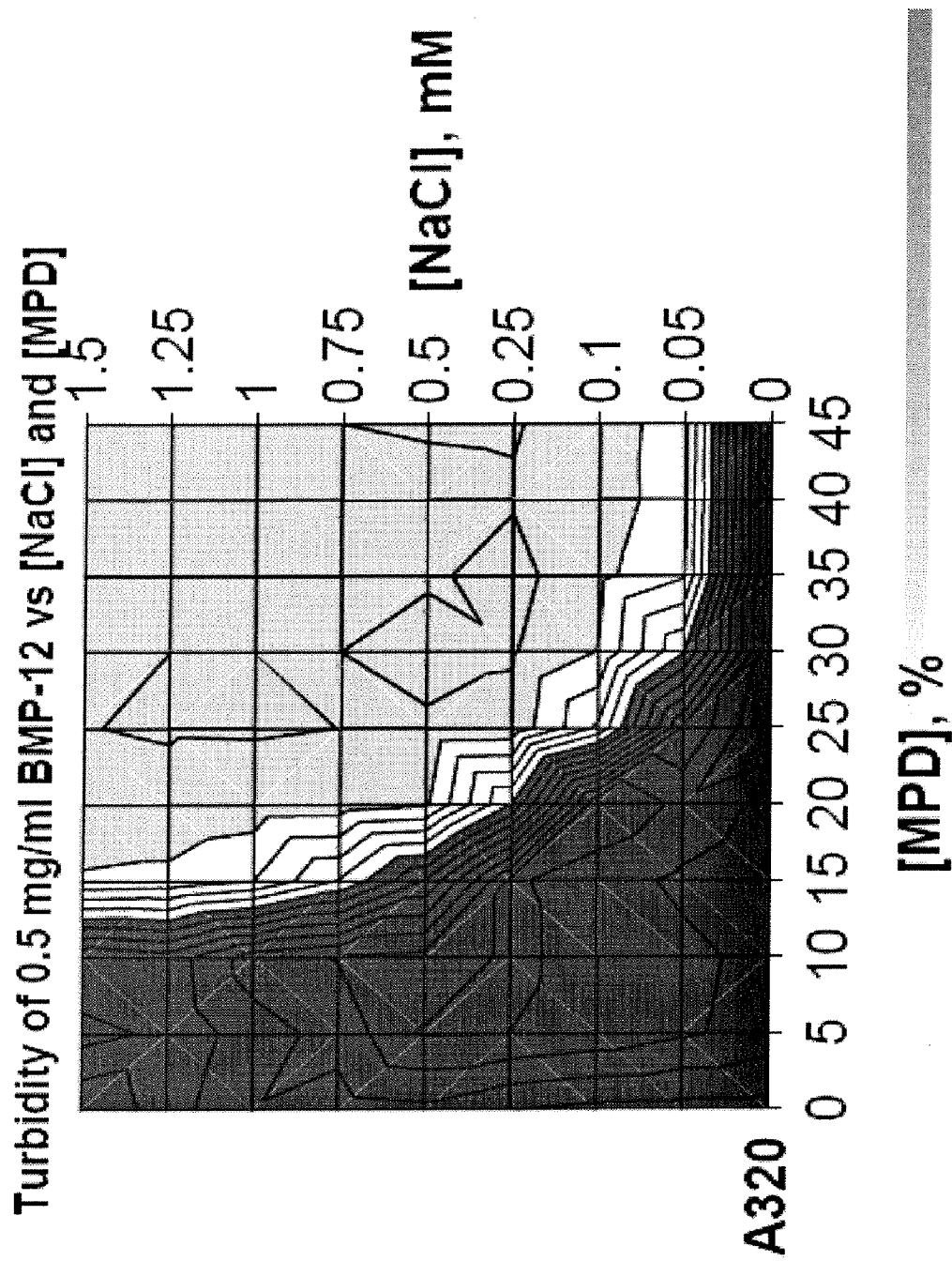
FIG. 13 is a graph illustrating the turbidity of solutions of 0.5 mg/mL BMP-12 with respect to concentrations of NaCl and 2-methyl-2,4-pentanediol in 50 mM Tris, pH 8.

BMP Solubility Screen—A Tecan liquid-handling robot was used to mix a master plate of reagents, 800 μL×1.25 concentration (for each solution; see Tables 2 and 3), each in 50 mM Tris buffer at pH 8. An eight-channel pipettor was used to transfer 80 μL of material from the master plate into a half-area UV microplate, from which $A_{320}$ was read from each sample to define a blank. A repeat-pipettor was used to add 20 μL of 2.5 mg/mL BMP-12 in 0.1% TFA to make a 0.5 mg/mL solution, which was then agitated at 14000 rpm. The UV absorption ($A_{320}$) was read and the blank absorption subtracted to determine solubility. The procedure was repeated with a wider range of 2-methyl-2,4-pentanediol (MPD) concentrations and a finer set of salt concentrations (Table 4). A graph comparing the turbidity of BMP-12 solutions with respect to NaCl and MPD concentrations is shown in FIG. 13.

TABLE 2

| | 1-Propanol, % | | | | | |
|---|---|---|---|---|---|---|
| NaCl, M | 0 | 2.5 | 5 | 10 | 15 | 25 |
| 0 | 1.724 | 1.848 | 2.134 | 2.000 | 3.172 | 1.419 |
| 0.1 | 1.745 | 2.135 | 2.212 | 1.945 | 3.199 | 0.104 |
| 0.25 | 1.804 | 2.397 | 2.300 | 2.105 | 1.392 | 0.022 |
| 0.5 | 1.953 | 2.170 | 1.629 | 1.313 | 0.305 | −0.001 |

TABLE 2-continued

| | 1-Propanol, % | | | | | |
|---|---|---|---|---|---|---|
| NaCl, M | 0 | 2.5 | 5 | 10 | 15 | 25 |
| 0.75 | 1.911 | 2.023 | 1.541 | 1.032 | 0.094 | −0.003 |
| 1 | 1.988 | 1.601 | 1.817 | 1.000 | 0.040 | −0.010 |
| 1.25 | 1.702 | 1.376 | 1.643 | 1.018 | 0.033 | 0.022 |
| 1.5 | 1.981 | 1.358 | 1.598 | 0.973 | 0.036 | 0.478 |

TABLE 3

| | 2-Methyl-2,4-pentanediol, % | | | | | |
|---|---|---|---|---|---|---|
| NaCl, M | 2.5 | 5 | 10 | 15 | 20 | 25 |
| 0 | 1.936 | 2.122 | 2.148 | 2.035 | 2.136 | 2.631 |
| 0.1 | 1.900 | 2.338 | 2.341 | 2.287 | 2.573 | 0.715 |
| 0.25 | 2.061 | 2.399 | 2.434 | 2.433 | 1.006 | 0.119 |
| 0.5 | 2.045 | 2.414 | 2.258 | 1.420 | 0.165 | 0.020 |
| 0.75 | 1.985 | 2.076 | 2.211 | 0.818 | 0.099 | 0.001 |
| 1 | 2.133 | 1.903 | 2.110 | 0.400 | 0.089 | −0.015 |
| 1.25 | 1.819 | 1.643 | 1.688 | 0.257 | 0.040 | −0.011 |
| 1.5 | 1.767 | 1.521 | 1.798 | 0.227 | 0.045 | 0.003 |

TABLE 4

| NaCl, M | 2-Methyl-2,4-pentanediol, % | | | | | | | | | |
|---|---|---|---|---|---|---|---|---|---|---|
| | 2.5 | 5 | 10 | 15 | 20 | 25 | 30 | 35 | 40 | 45 |
| 0.00 | 1.936 | 2.122 | 2.148 | 2.035 | 2.136 | 2.631 | 3.443 | 3.006 | 3.519 | 3.308 |
| 0.05 | n/a | n/a | n/a | n/a | n/a | 1.994 | 0.979 | 0.376 | 0.330 | 0.318 |
| 0.10 | 1.900 | 2.338 | 2.341 | 2.287 | 2.573 | 0.626 | 0.206 | 0.150 | 0.083 | 0.087 |
| 0.25 | 2.061 | 2.399 | 2.434 | 2.433 | 1.006 | 0.047 | −0.015 | −0.065 | 0.015 | −0.012 |
| 0.50 | 2.045 | 2.414 | 2.258 | 1.420 | 0.165 | 0.038 | −0.091 | 0.026 | 0.024 | −0.008 |
| 0.75 | 1.985 | 2.076 | 2.211 | 0.818 | 0.099 | 0.001 | | | | |
| 1.00 | 2.133 | 1.903 | 2.110 | 0.400 | 0.089 | −0.015 | | | | |
| 1.25 | 1.819 | 1.643 | 1.688 | 0.257 | 0.040 | −0.011 | | | | |
| 1.50 | 1.767 | 1.521 | 1.798 | 0.227 | 0.045 | 0.003 | | | | |

Example 13

Figure 14:
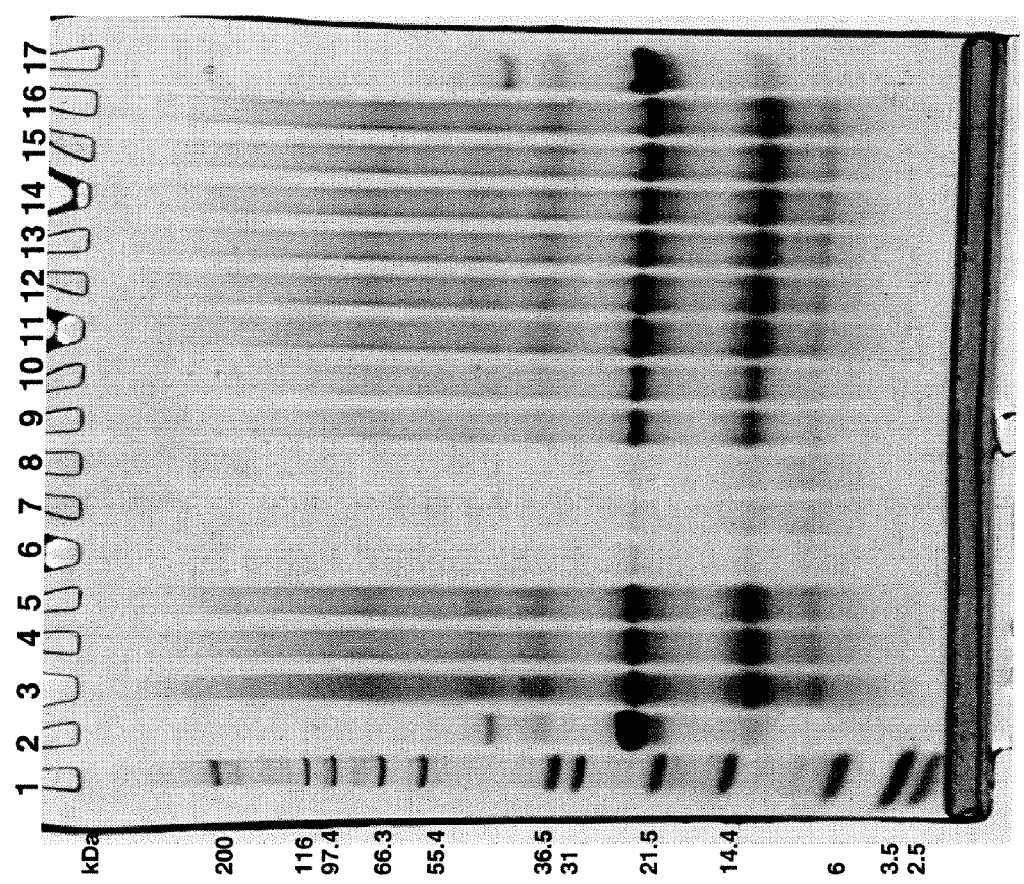
FIG. 14 is a photograph of a gel after SEC of the eluate from resins conjugated with BMP-finger peptides and loaded with BMP-12 under various conditions.

Affinity resins were coupled with the peptides listed in Table 5. The coupled resins, plus an unconjugated resin for use as a control, were suspended in 16% ethanol, 150 mM NaCl, and 20 mM Tris buffer at pH 7.5 at a 25% v/v ratio (e.g., 25% ethanol, 75% Tris buffer). A Tecan liquid-handling robot was employed to aliquot 200 μL of each slurry into one of eight rows of a 96 well polystyrene filter plate (0.45 μm hydrophilic filters, Whatman catalog number 770-1806). Spinning at 1200 g for 3 min removed the liquid phase, leaving 50 μL of wet resin on the filters. The resins were then equilibrated with the loading buffers listed in Table 6 (K is a coefficient characterizing the strength of protein binding to a particular resin in a particular buffer). A BMP-12 load plate was prepared by adding 40 μL of low molecular weight size exclusion chromatography (LMW SEC) solution (BEP, dialyzed in 0.1% TFA and concentrated to 3.76 mg/mL) to 260 μL of each loading buffer in a 96-well plate, resulting in 0.48 mg/mL of protein in each well. The resins were loaded by transferring 150 μL from the load plate to the filter plate and then incubating 20 min on a shaking platform to facilitate binding. The filter plate was spun down and the filtrate collected in a 96 well UV plate. The protein concentration in the filtrate, or flow-through, was calculated as $(A_{280}-A_{320})/1.3$. The filter plate was then washed with 150 μL of 100 mM acetic acid, followed by 150 μL of 4M guanidine-HCl and 50 mM sodium acetate at pH 4.0. The protein concentration was measured in the new filtrate as described above. As shown in Table 6, resins coupled to peptides 747, 747, 748 and 749 bound BMP12 with a high affinity in loading buffers 1-5. However, for peptides 750 and 751, the binding was strong in 25 mM MES at pH 6 but weak in 50 mM acetic acid with 0.1 M NaCl at pH 3.0, which can allow an efficient binding-elution process without the need for chaotrops or organic reagents. Flow-through and acetic acid elution samples from column 4 of the plate (loaded with MES pH 6) were analyzed on a gel (FIG. 14).

TABLE 5

| Peptide Name | ID | Peptide |
|---|---|---|
| BMP2 N-trun 1S | 751 | Ac-SDVGWNDWIVAPPGYHAFYSHGEK (SEQ ID NO: 17) |
| BMP2 N-trun | 750 | Ac-SDVGWNDWIVAPPGYHAFYCHGEK (SEQ ID NO: 18) |
| BMP12 N-trun_1S | 749 | Ac-ELGWDDWIIAPLDYEAYHSEGLK (SEQ ID NO: 19) |
| BMP5 | 748 | Ac-RDLGWQDWIIAPEGYAAFYSDGEK (SEQ ID NO: 20) |
| BMP2 Full | 747 | Ac-LYVDFSDVGWNDWIVAPPGYHAFYSHGEK (SEQ ID NO: 21) |
| BMP2 C-trunc_2 | 746 | Ac-LYV**SDVGWNDWIVK (SEQ ID NO: 22) |
| BMP2 N-trunc_2 | 745 | Ac-VAPPGYHAFYSHGEK (SEQ ID NO: 23) |

TABLE 6

| Load conditions* | Resin | 1<br>50 mM Acetic Acid, 0.1 M NaCl, pH 2.9 | 2<br>50 mM Acetic Acid, 0.1 M NaCl, pH 4.0 | 3<br>25 mM Na Acetate pH 5.0 | 4<br>25 mM MES pH 6.0 | 5<br>25 mM HEPES pH 7.0 | 6<br>1M CHES pH 9.7 | 10<br>50 mM Tris, 0.1 M NaCl, 40% MPD, pH 8.0 | 11<br>50 mM Tris, 0.25 M NaCl, 30% MPD, pH 8.0 | 12<br>50 mM Tris, 0.1 M NaCl, 20% MPD, pH 8.0 |
|---|---|---|---|---|---|---|---|---|---|---|
| Flow-through conc, mg/ml | Control | 0.425 | 0.408 | 0.410 | 0.397 | 0.396 | 0.686 | 0.488 | 0.482 | 0.467 |
| | 745 | 0.397 | 0.410 | 0.407 | 0.426 | 0.397 | 0.626 | 0.464 | 0.431 | 0.435 |
| | 746 | 0.150 | 0.052 | 0.070 | 0.029 | 0.162 | 0.710 | 0.505 | 0.515 | 0.486 |
| | 747 | 0.114 | 0.029 | 0.046 | 0.035 | 0.103 | 0.659 | 0.482 | 0.450 | 0.438 |
| | 748 | 0.106 | 0.023 | 0.024 | 0.022 | 0.055 | 0.626 | 0.407 | 0.375 | 0.383 |
| | 749 | 0.175 | 0.050 | 0.032 | 0.025 | 0.116 | 0.653 | 0.434 | 0.416 | 0.404 |
| | 750 | 0.337 | 0.164 | 0.163 | 0.037 | 0.290 | 0.577 | 0.423 | 0.342 | 0.364 |
| | 751 | 0.349 | 0.156 | 0.124 | 0.035 | 0.216 | 0.647 | 0.435 | 0.425 | 0.411 |

TABLE 6-continued

| Load conditions* | Resin | 1<br>50 mM Acetic Acid, 0.1 M NaCl, pH 2.9 | 2<br>50 mM Acetic Acid, 0.1 M NaCl, pH 4.0 | 3<br>25 mM Na Acetate pH 5.0 | 4<br>25 mM MES pH 6.0 | 5<br>25 mM HEPES pH 7.0 | 6<br>1M CHES pH 9.7 | 10<br>50 mM Tris, 0.1 M NaCl, 40% MPD, pH 8.0 | 11<br>50 mM Tris, 0.25 M NaCl, 30% MPD, pH 8.0 | 12<br>50 mM Tris, 0.1 M NaCl, 20% MPD, pH 8.0 |
|---|---|---|---|---|---|---|---|---|---|---|
| Flow-through K | Control | 0 | 1 | 1 | 1 | 1 | −1 | 0 | 0 | 0 |
| | 745 | 1 | 1 | 1 | 0 | 1 | −1 | 0 | 0 | 0 |
| | 746 | 7 | 25 | 18 | 47 | 6 | −1 | 0 | 0 | 0 |
| | 747 | 10 | 47 | 28 | 38 | 11 | −1 | 0 | 0 | 0 |
| | 748 | 11 | 59 | 57 | 62 | 23 | −1 | 1 | 1 | 1 |
| | 749 | 5 | 26 | 42 | 56 | 9 | −1 | 0 | 0 | 1 |
| | 750 | 1 | 6 | 6 | 36 | 2 | −1 | 0 | 1 | 1 |
| | 751 | 1 | 6 | 9 | 38 | 4 | −1 | 0 | 0 | 1 |
| 100 mM HAc elution conc, mg/ml | Control | 0.066 | 0.064 | 0.070 | 0.129 | 0.073 | | | | |
| | 745 | 0.058 | 0.057 | 0.073 | 0.104 | 0.077 | | | | |
| | 746 | 0.154 | 0.208 | 0.296 | 0.320 | 0.249 | | | | |
| | 747 | 0.123 | 0.147 | 0.274 | 0.324 | 0.255 | | | | |
| | 748 | 0.123 | 0.151 | 0.264 | 0.304 | 0.257 | | | | |
| | 749 | 0.098 | 0.175 | 0.275 | 0.321 | 0.280 | | | | |
| | 750 | 0.096 | 0.194 | 0.226 | 0.311 | 0.187 | | | | |
| | 751 | 0.102 | 0.219 | 0.285 | 0.355 | 0.254 | | | | |
| 100 mM HAc elution K | Control | 0 | 0 | 0 | −1 | 0 | | | | |
| | 745 | 1 | 1 | 0 | −1 | 0 | | | | |
| | 746 | 3 | 3 | 1 | 1 | 1 | | | | |
| | 747 | 6 | 6 | 2 | 1 | 1 | | | | |
| | 748 | 6 | 6 | 2 | 2 | 2 | | | | |
| | 749 | 6 | 4 | 2 | 1 | 1 | | | | |
| | 750 | 1 | 2 | 1 | 1 | 0 | | | | |
| | 751 | 1 | 1 | 1 | 1 | 0 | | | | |
| 4M Gnd, 50 mM NaAc pH 4 Strip Conc, mg/ml | Control | 0.029 | 0.023 | 0.025 | 0.031 | 0.021 | | | | |
| | 745 | 0.024 | 0.026 | 0.026 | 0.027 | 0.021 | | | | |
| | 746 | 0.135 | 0.162 | 0.100 | 0.070 | 0.068 | | | | |
| | 747 | 0.150 | 0.150 | 0.111 | 0.065 | 0.074 | | | | |
| | 748 | 0.177 | 0.229 | 0.140 | 0.091 | 0.105 | | | | |
| | 749 | 0.141 | 0.196 | 0.126 | 0.079 | 0.093 | | | | |
| | 750 | 0.044 | 0.087 | 0.072 | 0.060 | 0.046 | | | | |
| | 751 | 0.046 | 0.089 | 0.070 | 0.053 | 0.044 | | | | |
| Yield, % | Control | 108 | 103 | 105 | 116 | 102 | | | | |
| | 745 | 100 | 103 | 105 | 116 | 103 | | | | |
| | 746 | 91 | 88 | 97 | 87 | 100 | | | | |
| | 747 | 81 | 68 | 90 | 88 | 90 | | | | |
| | 748 | 85 | 84 | 89 | 87 | 87 | | | | |
| | 749 | 86 | 88 | 90 | 88 | 102 | | | | |
| | 750 | 100 | 93 | 96 | 85 | 109 | | | | |
| | 751 | 104 | 97 | 100 | 92 | 107 | | | | |

*Load conditions that developed precipitation: 50 mM HEPES, 0.5M NaCl, 25% 1-propanol, pH 7.0 50 mM Tris. 0.5 M NaCl, 25% IPA, pH 8.6 50 mM HEPES, 0.5M NACl, 25% tert-butanol, pH 7.0

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. An isolated peptide comprising the amino acid sequence of SEQ ID NO:1, SEQ ID NO:4, SEQ ID NO:5, SEQ ID NO:6, SEQ ID NO:7, SEQ ID NO:8, SEQ ID NO:9, SEQ ID NO:11, SEQ ID NO:12, SEQ ID NO:13, SEQ ID NO:14, SEQ ID NO:16, SEQ ID NO:17, SEQ ID NO:18, SEQ ID NO:19, SEQ ID NO:20, SEQ ID NO:21, SEQ ID NO:22, or SEQ ID NO:23.

2. A method of stabilizing a solution containing a protein in the TGF-β superfamily, comprising adding a peptide of claim 1 to the solution, wherein the ratio of the peptide to the protein is at least 1:1, 2:1, 5:1, 10:1, 20:1, or 30:1.

3. The method of claim 2, wherein the TGF-β superfamily protein is a BMP.

4. The method of claim 2, wherein the TGF-β superfamily protein is a growth differentiation factor (GDF).

5. A method of purifying a protein in the transforming growth factor beta (TGF-β) superfamily from a sample, comprising:
    providing a chromatography column containing a chromatography resin derivatized with a peptide of claim 1 through a covalent bond with the N- or C-terminus of the peptide;
    loading the column with the sample;
    and eluting the protein from the column.

6. The method of claim 5, wherein the TGF-β superfamily protein is a BMP.

7. The method of claim 5, wherein the TGF-β superfamily protein is a growth differentiation factor (GDF).

8. An isolated nucleic acid comprising a nucleotide sequence encoding the amino acid sequence of SEQ ID NO:1, SEQ ID NO:4, SEQ ID NO:5, SEQ ID NO:6, SEQ ID NO:7, SEQ ID NO:8, SEQ ID NO:9,
    SEQ ID NO:11, SEQ ID NO:12, SEQ ID NO:13, SEQ ID NO:14, SEQ ID NO:16, SEQ ID
    NO:17, SEQ ID NO:18, SEQ ID NO:19, SEQ ID NO:20, SEQ ID NO:21, SEQ ID NO:22, or SEQ ID NO:23.

* * * * *